US010016451B2

(12) United States Patent
Edelson et al.

(10) Patent No.: US 10,016,451 B2
(45) Date of Patent: Jul. 10, 2018

(54) NUCLEIC ACID NANOPARTICLES AND USES THEREFOR

(75) Inventors: Jonathan Edelson, Scarsdale, NY (US); Timothy Kotyla, Lowell, MA (US); Boke Zhang, Brighton, MA (US)

(73) Assignee: Anterios, Inc., New York, NY (US)

( * ) Notice: Subject to any disclaimer, the term of this patent is extended or adjusted under 35 U.S.C. 154(b) by 1528 days.

(21) Appl. No.: 12/671,693

(22) PCT Filed: May 30, 2008

(86) PCT No.: PCT/US2008/065329
§ 371 (c)(1),
(2), (4) Date: May 6, 2011

(87) PCT Pub. No.: WO2008/151022
PCT Pub. Date: Dec. 11, 2008

(65) Prior Publication Data
US 2011/0305734 A1    Dec. 15, 2011

Related U.S. Application Data

(60) Provisional application No. 60/941,187, filed on May 31, 2007.

(51) Int. Cl.
C12N 15/113     (2010.01)
A61K 31/7105    (2006.01)
A61K 9/00       (2006.01)
A61K 9/107      (2006.01)

(52) U.S. Cl.
CPC ........ *A61K 31/7105* (2013.01); *A61K 9/0014* (2013.01); *A61K 9/1075* (2013.01)

(58) Field of Classification Search
CPC .................................................. C12N 15/113
See application file for complete search history.

(56) References Cited

U.S. PATENT DOCUMENTS

| | | | |
|---|---|---|---|
| 4,172,149 A | 10/1979 | Pinto et al. | |
| 4,533,254 A | 8/1985 | Cook et al. | |
| 4,908,154 A | 3/1990 | Cook et al. | |
| 5,008,110 A | 4/1991 | Benecke et al. | |
| 5,152,923 A | 10/1992 | Weder et al. | |
| 5,374,614 A | 12/1994 | Behan et al. | |
| 5,401,243 A | 3/1995 | Borodic | |
| 5,470,577 A * | 11/1995 | Gilchrest et al. | 424/450 |
| 5,502,045 A | 3/1996 | Miettinen et al. | |
| 5,510,118 A | 4/1996 | Bosch et al. | |
| 5,576,016 A | 11/1996 | Amselem et al. | |
| 5,591,767 A | 1/1997 | Mohr et al. | |
| 5,629,021 A | 5/1997 | Wright | |
| 5,651,991 A | 7/1997 | Sugiyama et al. | |
| 5,652,274 A | 7/1997 | Martin | |
| 5,660,858 A | 8/1997 | Parikh et al. | |
| 5,670,484 A | 9/1997 | Binder | |
| 5,672,358 A | 9/1997 | Tabibi et al. | |
| 5,683,712 A | 11/1997 | Cavazza | |
| 5,753,241 A | 5/1998 | Ribier et al. | |
| 5,766,605 A | 6/1998 | Sanders et al. | |
| 5,851,452 A | 12/1998 | Vallet Mas et al. | |
| 5,858,410 A | 1/1999 | Muller et al. | |
| 5,925,341 A | 7/1999 | Cervantes et al. | |
| 5,932,562 A | 8/1999 | Ostlund, Jr. | |
| 5,948,433 A | 9/1999 | Burton et al. | |
| 5,965,154 A | 10/1999 | Haralambopoulos | |
| 5,994,414 A | 11/1999 | Franco et al. | |
| 6,007,856 A | 12/1999 | Cox et al. | |
| 6,010,715 A | 1/2000 | Wick et al. | |
| 6,039,936 A | 3/2000 | Restle et al. | |
| 6,165,500 A | 12/2000 | Cevc | |
| 6,224,853 B1 | 5/2001 | Steel et al. | |
| 6,265,180 B1 | 7/2001 | Zuelli et al. | |
| 6,274,150 B1 | 8/2001 | Simonnet et al. | |
| 6,312,708 B1 | 11/2001 | Donovan | |
| 6,358,917 B1 | 3/2002 | Carruthers et al. | |
| 6,387,411 B2 | 5/2002 | Bruce et al. | |
| 6,429,189 B1 | 8/2002 | Borodic | |
| 6,455,058 B1 | 9/2002 | Sun et al. | |
| 6,558,941 B2 | 5/2003 | Zuelli et al. | |
| 6,573,241 B1 | 6/2003 | Bigalke et al. | |
| 6,589,588 B1 | 7/2003 | Wester et al. | |
| 6,620,419 B1 | 9/2003 | Lintner | |
| 6,623,780 B1 | 9/2003 | Stevens et al. | |
| 6,632,440 B1 | 10/2003 | Quinn et al. | |

(Continued)

FOREIGN PATENT DOCUMENTS

CA     02067754 A1   2/1992
CA     2465123 A1    5/2003
(Continued)

OTHER PUBLICATIONS

Rhee et al. International Journal of Pharmaceutics 228 2001, 161-170.*
Solans et al. Current Opinion in Colloid & Interface Science 10 2005, 102-110.*
Croda Inc., Pharmaceutical Technology, 3 pages (2005), Retrieved online: http://www.pharmtech.com/pharmtech/Corporate=Capabilities/Croda-Inc/ArticleStandard/Article/detail/399061.
Barr et al., Different Substrate Recognition Requirements for cleavage of Synaptobrevin-2 by Clostridium baratii and Clostridium botulinum, Applied and Environmental Microbiology p. 1301-1308, 2011.
Bauerova et al., Chemical enhancers for transdermal drug transport, European J Drug Metabolism and Pharmacokinetics 26(1/2):85-94 (2001).
Bhartiya et al., Enhanced Wound Healing in Animal Models by Interferon and an Interferon Inducer, J Cell Physiol 150:312 (1992).

(Continued)

*Primary Examiner* — Brian A Whiteman
(74) *Attorney, Agent, or Firm* — McCarter & English, LLP; Marcie B. Clarke; Joshua J. Galgano

(57) ABSTRACT

The present invention provides nanoparticle compositions including one or more nucleic acids. The present invention achieves delivery (particularly transdermal delivery) of such nucleic acids without the need for nucleic acid modification, or for use of chemical or mechanical abrasion or disruption of skin.

32 Claims, No Drawings

(56) References Cited

U.S. PATENT DOCUMENTS

| | | | |
|---|---|---|---|
| 6,670,322 B2 | 12/2003 | Goodnough et al. |
| 6,688,311 B2 | 2/2004 | Hanin |
| 6,720,001 B2 | 4/2004 | Chen et al. |
| 6,835,395 B1 | 12/2004 | Semple et al. |
| 6,835,895 B1 | 12/2004 | Asai et al. |
| 6,861,066 B2 | 3/2005 | Van de Casteele |
| 6,869,610 B2 | 3/2005 | Aoki et al. |
| 6,890,560 B2 | 5/2005 | Seo et al. |
| 6,902,737 B2 | 6/2005 | Quemin |
| 6,939,852 B2 | 9/2005 | Graham |
| 6,974,578 B1 | 12/2005 | Aoki et al. |
| 6,974,579 B2 | 12/2005 | Brin et al. |
| 7,001,602 B2 | 2/2006 | Schmidt |
| 7,226,605 B2 | 6/2007 | Suskind et al. |
| 7,228,259 B2 | 6/2007 | Freund |
| 7,255,865 B2 | 8/2007 | Walker |
| 7,384,918 B2 | 6/2008 | Graham |
| 7,419,996 B2 | 9/2008 | Chow et al. |
| 7,507,419 B2 | 3/2009 | Coleman, III |
| 7,763,663 B2 | 7/2010 | McCarthy et al. |
| 8,318,181 B2 | 11/2012 | Edelson et al. |
| 2002/0015721 A1 | 2/2002 | Slimonnet et al. |
| 2002/0048596 A1 | 4/2002 | Cevc |
| 2002/0098215 A1 | 7/2002 | Douin et al. |
| 2002/0107199 A1 | 8/2002 | Walker |
| 2002/0155084 A1 | 10/2002 | Roessler et al. |
| 2002/0165179 A1 | 11/2002 | Baker |
| 2003/0072801 A1 | 4/2003 | Curatolo et al. |
| 2003/0077240 A1 | 4/2003 | LeGrow et al. |
| 2003/0086888 A1 | 5/2003 | LeGrow et al. |
| 2003/0108597 A1 | 6/2003 | Chancellor et al. |
| 2003/0113349 A1 | 6/2003 | Coleman |
| 2003/0138465 A9 | 7/2003 | Douin et al. |
| 2003/0157138 A1 | 8/2003 | Eini et al. |
| 2003/0194412 A1 | 10/2003 | Baker et al. |
| 2003/0206955 A1 | 11/2003 | Sonneville-Aubrun et al. |
| 2003/0211140 A1 | 11/2003 | Mantripragada et al. |
| 2003/0224020 A1 | 12/2003 | Zabudkin et al. |
| 2004/0003324 A1 | 1/2004 | Uhlig et al. |
| 2004/0005370 A1 | 1/2004 | Breton |
| 2004/0009180 A1 | 1/2004 | Donovan |
| 2004/0009936 A1 | 1/2004 | Tang et al. |
| 2004/0028635 A1 | 2/2004 | Chauvierre et al. |
| 2004/0033202 A1 | 2/2004 | Cooper et al. |
| 2004/0033241 A1 | 2/2004 | Donovan |
| 2004/0037853 A1 | 2/2004 | Borodic |
| 2004/0048836 A1 | 3/2004 | Wilmott |
| 2004/0081688 A1 | 4/2004 | Del Curto et al. |
| 2004/0115159 A1 | 6/2004 | Tadlock et al. |
| 2004/0115727 A1 | 6/2004 | Steward et al. |
| 2004/0126397 A1 | 7/2004 | Aoki et al. |
| 2004/0127661 A1 | 7/2004 | Kaspar et al. |
| 2004/0132667 A1 | 7/2004 | Lintner |
| 2004/0151741 A1 | 8/2004 | Borodic |
| 2004/0191330 A1 | 9/2004 | Keefe et al. |
| 2004/0229038 A1 | 11/2004 | Cooper et al. |
| 2004/0234588 A1* | 11/2004 | Lu et al. ............ 424/450 |
| 2004/0235770 A1* | 11/2004 | Davis et al. ............ 514/44 |
| 2004/0258747 A1 | 12/2004 | Ponzoni et al. |
| 2004/0258758 A1 | 12/2004 | Gustow et al. |
| 2005/0038096 A1 | 2/2005 | Chow et al. |
| 2005/0048088 A1 | 3/2005 | Zulli et al. |
| 2005/0065090 A1 | 3/2005 | Ludin et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0079228 A1 | 4/2005 | Jaiswal et al. |
| 2005/0096340 A1 | 5/2005 | Zhang et al. |
| 2005/0118254 A1 | 6/2005 | Choi et al. |
| 2005/0123897 A1 | 6/2005 | Cevc et al. |
| 2005/0124378 A1 | 6/2005 | Griffith et al. |
| 2005/0136024 A1 | 6/2005 | Stockel |
| 2005/0142150 A1 | 6/2005 | Graham |
| 2005/0147688 A1 | 7/2005 | Russell |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0208083 A1 | 9/2005 | Annis |
| 2005/0214325 A1 | 9/2005 | David |
| 2005/0222071 A1* | 10/2005 | Duranton ............ A61K 8/606 514/44 A |
| 2005/0226842 A1 | 10/2005 | Douin et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0073208 A1 | 4/2006 | First |
| 2006/0084353 A1 | 4/2006 | Wong et al. |
| 2006/0093624 A1 | 5/2006 | Graham |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0182794 A1 | 8/2006 | Modi |
| 2006/0188525 A1 | 8/2006 | Donovan |
| 2007/0009555 A1 | 1/2007 | Borodic |
| 2007/0036831 A1 | 2/2007 | Baker |
| 2007/0104743 A1 | 5/2007 | Lehtola et al. |
| 2007/0116723 A1 | 5/2007 | Coleman |
| 2007/0148194 A1 | 6/2007 | Amiji et al. |
| 2007/0178121 A1 | 8/2007 | First et al. |
| 2007/0253911 A1 | 11/2007 | Tamarkin et al. |
| 2007/0292359 A1 | 12/2007 | Friedman et al. |
| 2008/0050352 A1 | 2/2008 | Webb et al. |
| 2008/0206155 A1 | 8/2008 | Tamarkin et al. |
| 2008/0207737 A1 | 8/2008 | Zinger |
| 2008/0274195 A1 | 11/2008 | Nicolosi et al. |
| 2009/0041680 A1 | 2/2009 | Tamarkin et al. |
| 2009/0306198 A1 | 12/2009 | Nicolosi et al. |
| 2010/0040883 A1 | 2/2010 | McCarthy et al. |
| 2010/0137357 A1 | 6/2010 | Koleng et al. |
| 2010/0150994 A1 | 6/2010 | Kotyla |
| 2010/0172943 A1 | 7/2010 | Edelson et al. |
| 2010/0183726 A1 | 7/2010 | Nicolosi et al. |
| 2010/0233251 A1 | 9/2010 | Von Andrian et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2011/0212157 A1 | 9/2011 | Edelson et al. |
| 2012/0164182 A1 | 6/2012 | Edelson et al. |
| 2012/0328525 A1 | 12/2012 | Edelson et al. |
| 2012/0328549 A1 | 12/2012 | Edelson et al. |
| 2012/0328701 A1 | 12/2012 | Edelson et al. |

FOREIGN PATENT DOCUMENTS

| | | |
|---|---|---|
| CA | 2543722 A1 | 5/2005 |
| CA | 2554052 A1 | 8/2005 |
| CA | 2494473 C | 6/2007 |
| CA | 2631927 A1 | 4/2008 |
| CA | 2688415 A1 | 12/2008 |
| DE | 102004016710 A1 | 10/2005 |
| EP | 0315079 A1 | 5/1989 |
| EP | 0572080 B1 | 11/1995 |
| EP | 1080720 A1 | 3/2001 |
| EP | 0770422 B1 | 9/2002 |
| EP | 1586336 A1 | 10/2005 |
| EP | 1652515 A1 | 5/2006 |
| EP | 1249232 B1 | 10/2006 |
| EP | 1784163 A1 | 5/2007 |
| EP | 1345597 B1 | 10/2007 |
| FR | 2849375 A1 | 7/2004 |
| JP | 1990000203 | 1/1990 |
| JP | 1995285863 | 10/1995 |
| JP | 1996507515 | 8/1996 |
| JP | 2001513331 A | 9/2001 |
| JP | 2002308728 A | 10/2002 |
| JP | 2003527411 A | 9/2003 |
| JP | 2006273821 A | 10/2006 |
| WO | WO-1990011364 A1 | 10/1990 |
| WO | WO-9318752 A1 | 9/1993 |
| WO | WO-9420072 A1 | 9/1994 |
| WO | WO-9522973 A1 | 8/1995 |
| WO | WO-1995035157 A1 | 12/1995 |

(56) References Cited

FOREIGN PATENT DOCUMENTS

| | | |
|---|---|---|
| WO | 98/51278 A2 | 11/1998 |
| WO | WO-9907238 A2 | 2/1999 |
| WO | WO-199944594 A1 | 9/1999 |
| WO | WO-0007621 A2 | 2/2000 |
| WO | WO-98/51278 A3 | 6/2000 |
| WO | WO-0038653 A1 | 7/2000 |
| WO | WO-0110413 A2 | 2/2001 |
| WO | WO-01070197 A2 | 9/2001 |
| WO | WO-0188019 A1 | 11/2001 |
| WO | WO-0239979 A1 | 5/2002 |
| WO | WO-02051390 A2 | 7/2002 |
| WO | WO-02056866 A1 | 7/2002 |
| WO | WO-02080864 A1 | 10/2002 |
| WO | WO-03000243 A1 | 1/2003 |
| WO | WO-03011333 A1 | 2/2003 |
| WO | WO-03037933 A2 | 5/2003 |
| WO | WO-2003092585 A2 | 11/2003 |
| WO | WO-03101483 A1 | 12/2003 |
| WO | WO-2004006954 A2 | 1/2004 |
| WO | WO-2004076634 A2 | 9/2004 |
| WO | WO-2004084839 A2 | 10/2004 |
| WO | WO-2005013938 A1 | 2/2005 |
| WO | WO-2005020962 A1 | 3/2005 |
| WO | WO-2005023282 A1 | 3/2005 |
| WO | WO-2005027872 A2 | 3/2005 |
| WO | WO-2005042539 A1 | 5/2005 |
| WO | WO-2005058370 A1 | 6/2005 |
| WO | WO-05063377 A1 | 7/2005 |
| WO | WO-05070394 A2 | 8/2005 |
| WO | WO-05084361 A2 | 9/2005 |
| WO | WO-2005082514 A2 | 9/2005 |
| WO | WO-05102285 A1 | 11/2005 |
| WO | WO-2006005910 A2 | 1/2006 |
| WO | WO-2006028339 A1 | 3/2006 |
| WO | WO-2006050926 A2 | 5/2006 |
| WO | WO-2006084353 A1 | 8/2006 |
| WO | WO-2006094263 A2 | 9/2006 |
| WO | WO-2006138127 A2 | 12/2006 |
| WO | WO-2007041664 A1 | 4/2007 |
| WO | WO-2007046102 A2 | 4/2007 |
| WO | WO-2007089454 A2 | 8/2007 |
| WO | WO-2007103555 A2 | 9/2007 |
| WO | WO-2007149868 A2 | 12/2007 |
| WO | WO-08010788 A2 | 1/2008 |
| WO | WO-2008038147 A2 | 4/2008 |
| WO | WO-2008045107 A2 | 4/2008 |
| WO | WO-2008070538 A2 | 6/2008 |
| WO | WO2008074885 A2 * | 6/2008 |
| WO | WO-2008077641 A1 | 7/2008 |
| WO | WO-2008140594 A2 | 11/2008 |
| WO | WO-2008151022 A2 | 4/2009 |
| WO | WO-2009158687 A1 | 12/2009 |
| WO | WO-2010087964 A2 | 8/2010 |

OTHER PUBLICATIONS

Bos and Meinardi, The 500 Dalton rule for the skin penetration of chemical compounds and drugs, Exp Dermatol 9:165-169 (2000).
Brewster, Delivering Anti-aging Actives, Cosmetics and Toiletries, 120(6):30, 32-34 (2005).
Chen et al., Transdermal protein delivery by a coadministered peptide identified via phage display, Nature Biotechnology 24(4):455-459 (2006).
Cocconi et al., Treatment of Metastatic Malignant Melanoma with Dacarbazine Plux Tamoxifen, New England J Medicine 327(8):516-23 (1992).
De Campo et al., Five-component food-grade microemulsions: Structural characterization by SANS, J Colloid and Interface Science, 274:251-267 (2004).
De Paiva and Dolly, Light chain of botulinum nerotoxin is active in mammalian motor nerve terminals when delivered via liposomes, FEBS 277(1,2):171-174 (1990).
Delgado-Charro et al., Delivery of a hydrophilic solute through the skin from novel microemulsion systems, Eur J Pharmaceutics and Biopharmaceutics 43[1]:37-42 (1997).
Examination Report for EP 07874325.9, 8 pages (dated Apr. 5, 2012).
Examination Report for SG 200903663-3, 4 pages (dated Oct. 11, 2011).
Extended European Search Report for EP 12160402.9, 4 pages (dated Aug. 6, 2012).
Helene et al., Control of Gene Expression by Triple Helix-Forming Oligonucleotides, Ann N.Y. Acad Sci 660:27 (1992).
Helene, The anti-gene strategy: control of gene expression by triplex-forming-oligonucleotides, Anti-Cancer Drug Des 6:569-584 (1991).
International Preliminary Report on Patentability for PCT/US2006/035343, 5 pages (dated Mar. 18, 2008).
International Preliminary Report on Patentability for PCT/US2007/086018, 7 pages (dated Jun. 3, 2009).
International Preliminary Report on Patentability for PCT/US2008/065329, 8 pages (dated Dec. 1, 2009).
International Preliminary Report on Patentability for PCT/US2009/048972, 6 pages (dated Jan. 5, 2011).
International Search Report for PCT/US2006/026918, 4 pages (dated Jun. 19, 2008).
International Search Report for PCT/US2006/035343, 1 page (dated Aug. 15, 2007).
International Search Report for PCT/US2006/046236, 3 pages (dated Jun. 17, 2008).
International Search Report for PCT/US2007/086018, 5 pages (dated Sep. 17, 2008).
International Search Report for PCT/US2007/086040, 7 pages (dated Feb. 9, 2010).
International Search Report for PCT/US2009/048972, 5 pages (dated Dec. 1, 2009).
International Search Report for PCT/US2012/022276, 6 pages (dated Jul. 19, 2012).
International Search Report for PCT/US2012/022277, 4 pages (dated Jul. 6, 2012).
International Search Report for PCT/US2012/022278, 4 pages (dated Mar. 23, 2012).
International Search Report for PCT/US2012/022279, 7 pages (dated Nov. 29, 2012).
International Search Report for PCT/US2012/022280, 4 pages (dated Apr. 27, 2012).
International Search Report for PCT/US2012/022281, 4 pages (dated Apr. 24, 2012).
Izquierdo et al., The influence of surfactant mixing ration on nano-emulsion formation by the pit method, J Colloid and Interface Sci. 285:388-394 (2004).
Kakumanu et al., A Nanoemulsion Formulation of Dacarbazine Reduces Tumor Size in a Xenograft Mouse Epidermoid Carcinoma Model Compared to Dacarbazine Suspension, Nanomedicine: NBM 7(3):277-283 (2011).
Katayama et al., A Pentapeptide from Type I Procollagen Promotes Extracellular Matrix Production, J Biol Chem 268(14):9941-9944 (1993).
Keen et al., Botulinum Toxin A for Hyperkinetic Facial Lines: Results of a Double-Blind, Placebo-Controlled Study, Plastic and Reconstructive Surgery, 94(1):94-9 (1994).
Kitson, Drugs Used for Skin Diseases, Published in Dermatologic, Cosmeceutic, and Cosmetic Development Therapeutic and Novel Approaches, Ed Walters and Roberts 11-20 (2008).
Kotyla et al., Increased bioavailability of a transdermal application of a nano-sized emulsion preparation, International Journal of Pharmaceutics 347:144-148 (2008).
Kronberg et al., Preparation and Evaluation of Sterically Stabilized Liposomes: Colloidal Stability, Serum Stability, Macrophage Uptake, and Toxicity, J Pharmaceutical Sciences 79(8):667-671 (1990).
Kuo et al., Nanomulsions of an Anti-Oxidant Synergy Formulation Containing Gamma Tocopherol Have Enhanced Bioavailability and Anti-Inflammatory Properties, Int'l J Pharmaceutics 363:206-213 (2008).

(56) References Cited

OTHER PUBLICATIONS

Ludewig and Hoffmann, Adoptive Immunotherapy Methods and Protocols, Humana Press Inc., NJ 393 (2005).
Lupo, Cosmeceutical Peptides, Dermatologic Surgery 31:832-836 (2005).
Maher, DNA Triple-Helix Formation: An Approach to Artificial Gene Repressors?, BioEssays 14:807 (1992).
Montecucco et al., Effect of pH on the interaction of botulinum neurotoxins A, B and E with liposomes, Biochem J 259:47-53 (1989).
Morel et al., Incorporation in liposheres of {D-Trp-6}LHRH, Int'l J Pharmaceutics 105(2):R01-R03 (1994).
Poste et al., Lipid Vesicles as Carriers for Introducing Biologically Active Materials into Cells, Methods in cell biology 14:34 (1976).
PTO892 mailed Dec. 11, 2012, 1 page, U.S. Appl. No. 13/356,621.
Robinson, et al., Topical palmitoyl pentapeptide provides improvement in photoaged human facial skin, Int'l J Cosmetic Science 24:155-160 (2005).
Santiago et al., Topical Application of a Peptide Inhibitor of Transforming Growth Factor-β1 Ameliorates Bleomycin-Induced Skin Fibrosis, J Investigative Dermatorlogy 125:450-455 (2005).
Sarver et al., Ribozymes as Potential Anti-HIV-1 Therapeutic Agents, Science 247:1222-1225 (1990).
Schmalfuβ et al., Modification of drug penetration into human skin using microemulsions, J Controlled Release 46(3):279-285 (1997).
Search Report for AU2007329579, 3 pages (dated Jun. 1, 2012).
Search Report for AU2007353340, 2 pages (dated May 28, 2012).
Search Report for SG 200903662-5, 8 pages (dated Oct. 29, 2010).
Search Report for SG 200903663-3, 8 pages (dated Oct. 12, 2010).
Shone et al., A 50-kDa fragment from the NH2-terminus of the heavy subunit of *Clostridium botulinum* type A neurotoxin forms channels in lipid vesicles, Eur J Biochem 167:175-180 (1987).
Supplementary European Search Report for Application No. EP06851782, dated Jul. 3, 2012.
Tadros et al., Formation and stability of nano-emulsions, Advances in Colloid and Interface Science 108:109-303-318 (2004).
Tagne et al., Nanoemulsion Preparations of the Anticancer Drug Dacarbazine Significantly Increase Its Efficacy in Xenograft Mouse Melanoma Model, Molecular Pharmaceutics 5(6):1055-1063 (2008).
Trotta et al., Elastic Liposomes for Skin Delivery of Dipotassium Glycyrrhizinate, Int'l J Pharmaceutics 241:319-327 (2002).
Verma et al., Particle size of liposomes influences dermal delivery of substances into skin, Int'l J Pharmaceutics 141-151 (2003).
Wang et al., Enhancing effect of Labrafac Lipophile WL 1349 on oral bioavailability of hydroxysafflor yellow A in rats, International Journal of Pharmaceutics 358:198-204 (2008).
Written Opinion for PCT/US2007/086018, 6 pages (dated Sep. 17, 2008).
Written Opinion for PCT/US2007/086040, 12 pages (dated Feb. 9, 2010).
Written Opinion for PCT/US2008/065329, 7 pages (dated Mar. 12, 2009).
Written Opinion for PCT/US2009/048972, 5 pages (dated Dec. 1, 2009).
Written Opinion for PCT/US2012/022276, 9 pages (dated Jul. 19, 2012).
Written Opinion for PCT/US2012/022277, 6 pages (dated Jul. 6, 2012).
Written Opinion for PCT/US2012/022279, 7 pages (dated Nov. 29, 2012).
Written Opinion for PCT/US2012/022280, 7 pages (dated Apr. 27, 2012).
Written Opinion for PCT/US2012/022281, 6 pages (dated Apr. 24, 2012).
Written Opinion for PCT/US20120/22278, 7 pages (dated Mar. 23, 2012).
Written Opinion for SG 200903663-3, 7 pages (dated Oct. 12, 2010).
Written Opinion for SG 201009039-7, 6 pages (dated Mar. 12, 2012).
Written Opinion for SG200903662-5, 4 pages (dated Oct. 29, 2010).
Wu et al., Topical Transfection Using Plasmid DNA in a Water-in-Oil Nanoemulsion, Int J Pharmceutics 221(1/02):23-34 (2001).
Wu et al., Topical Transport of Hydrophilic Compounds Using Water-in-Oil Nanoemulsions, Int. J. Pharmaceutics, 220:63-75 (2001).
International Preliminary Report on Patentability for PCT/US2012/022276, 10 pages (dated Aug. 8, 2013).
International Preliminary Report on Patentability for PCT/US2012/022277, 7 pages (dated Aug. 8, 2013).
International Preliminary Report on Patentability for PCT/US2012/022278, 8 pages (dated Aug. 8, 2013).
International Preliminary Report on Patentability for PCT/US2012/022279, 9 pages (dated Aug. 8, 2013).
International Preliminary Report on Patentability for PCT/US2012/022280, 8 pages (dated Aug. 8, 2013).
International Preliminary Report on Patentability for PCT/US2012/022281, 7 pages (dated Aug. 8, 2013).
Badea et. al., In vivo cutaneous interferon-γ gene delivery using novel dicationic (gemini) surfactant-plasmid complexes, the Journal of Gene Medicine, 7:1200-1214 (2005).
Hickerson et al., SiRNA-Mediated Selective Inhibition of Mutant Keratin mRNAs Responsible for the Skin Disorder Pachyonychia Congenita, Ann. N.Y. Acad. Sci., 1082:56-61 (2006).
Badea et al., "In vivo cutaneous interferon-γ gene delivery using novel dicationic (gemini) surfactant-plasmid complexes", The Journal of Gene Medicine, 7:1200-1214 (2005).
Choi et al., "Percutaneous Absorption", Fourth Edition, vol. 155, Bronaugh and Maibach ed., Taylor and Francis, Boca Ratonm Florida, 2005, Index and Table of contents only, 33 pages.
Hickerson et al., "SiRNA-Mediated Selective Inhibition of Mutant Keratin mRNAs Responsible for the Skin Disorder Pachyonychia Congenita", Ann. N.Y. Acad. Sci., 1082:56-61 (2006).
Lin et al., "Delivery of plasmid DNA expression vector for karatinocyte growth factor-1 using electroporation to improve cutaneous wound healing in a septic rat model", Wound Repair and Regeneration, 14:618-624 (2006).
International Search Report for PCT/US2008/065329, dated Mar. 12, 2009.
Dalgleish et al., The characterization of small emulsion droplets made from milk proteins and triglyceride oil, Colloids and Surfaces, 123-124:145-153 (May 15, 1997).
PTO892, 1 page (Feb. 19, 2013).
Supplementary European Search Report for EP06851414.0, 8 pages (dated Oct. 1, 2012).
Teixeira et al., "Submicron Cationic Emulsions as a New Delivery System for Oligonucleotides," Pharmaceutical Research 16(1): 30-6 (1999).

\* cited by examiner

NUCLEIC ACID NANOPARTICLES AND USES THEREFOR

CROSS-REFERENCE TO RELATED APPLICATIONS

This application claims the benefit under 35 U.S.C. § 371 of International Application Number PCT/US2008/65329 (published on Dec. 11, 2008, as PCT publication number WO 2008/151022), filed May 30, 2008 ("the '329 application"), which claims priority under 35 U.S.C. § 119(e) to U.S. provisional patent application, U.S. Ser. No. 60/941,187, filed May 31, 2007 ("the '187 application"). The entire contents of the '187 application and the '329 application are incorporated herein by reference.

SEQUENCE LISTING

In accordance with 37 C.F.R. § 1.52(e)(5), a Sequence Listing in the form of a text file (entitled "Sequence_Listing," created on Feb. 1, 2010 and 10 kilobytes) is incorporated herein by reference in its entirety.

BACKGROUND OF THE INVENTION

Nucleic acids have been shown to have beneficial cosmetic and therapeutic effects on the skin. In experimental models, nucleic acids, such as cDNA coding for keratinocyte growth factor-1 (KGF-1) have been shown to improve wound healing (Lin et al., 2006, *Wound Repair Regen.*, 14:618). Similarly, nucleic acid coding for interferon gamma have been shown to stimulate interferon production which inhibits collagen synthesis in the skin and has the potential to treat scleroderma, a tissue connective disease (Badea et al., 2005, *J. Gene Med.*, 7:1200). In experimental models, siRNA targeting genes that code for the production of keratin in the skin were shown to inhibit these genes and have the potential to be used to treat the skin disorder pachyonychia congenita (Hickerson et al., 2006, *Ann. N.Y. Acad. Sci.*, 1082:56).

However, a problem in achieving the potential cosmetic and therapeutic effects of these nucleic acids in humans has been the transdermal delivery of these molecules across the outer skin layer of the skin (i.e., stratum corneum) to the site of biological action, such as the epidermis and dermis, deeper underlying tissue, and/or remote sites within the body (Choi et al., In: *Percutaneous Absorption*, 4$^{th}$ Ed., Bronaugh and Maibach, ed., Taylor & Francis, Boca Raton, Fla., 2005). The stratum corneum is an effective physical barrier that prevents transdermal penetration of molecules such as nucleic acids. Skin enzymes can also act to destroy the nucleic acids through enzymatic degradation (Choi et al., supra).

Attempts have been made to chemically modify nucleic acids to prevent such degradation, but such modification typically impairs the biological activity of the agent and/or induces unfavorable immune system reactions. Chemical modifications are also disadvantageous because they are expensive and time-consuming.

Some methods have been used to attempt to improve transdermal penetration of nucleic acids, including tape-stripping the outer layer of the skin, electroporation or iontophoresis of the skin, use of semi-solid formulations (e.g., creams, etc.), chemical penetration enhancers which degrade the stratum corneum, and/or nonionic liposomes (Choi et al., supra). Each of methods has one or more disadvantages, such as damaging the outer layer of the skin (which can be painful and irritating to the patient), having a complexity of treatment that deters use by a physician and/or patients, increasing the complexity and related cost of manufacture, and/or potentially impairing the biological activity of the nucleic acids.

Thus, there is a need in the art for methods of transdermal delivery of nucleic acids (e.g., polynucleotides and nucleic acid residues) that are simple to use, that are cost-efficient, that do not damage the outer layer of the skin, that protect against enzymatic degradation without inducing immune reactions, that do not impair the biological activity of the nucleic acid to be delivered, and/or that may enhance delivery to the site of biological action in the target tissue.

SUMMARY OF THE INVENTION

The present invention describes nanoparticle compositions. In some embodiments, nanoparticle compositions incorporate one or more unmodified and/or modified polynucleotides (up to 50 nucleotides long) and/or nucleic acid residues (e.g., nucleotides and/or nucleosides) that are biologically active agents in the skin (e.g., epidermis and/or dermis), sub-cutaneous tissue (e.g., adipose tissue), contiguous muscles, and/or distant tissues (e.g., organs such as lungs, liver, etc.).

Nanoparticles in accordance with the invention (e.g., nanoparticles that incorporate unmodified and/or modified polynucleotides) can be applied to the skin of a subject. In some embodiments, nanoparticles achieve delivery (in particular, transdermal delivery) of incorporated nucleic acids (e.g., polynucleotides and/or nucleic acid residues) to the subject.

Nanoparticles in accordance with the invention can be applied to the skin as a simple suspension or dispersion or mixed with one or more excipients and prepared as a formulation such as, but not limited to, a skin softener, nutrition lotion, cleansing lotion, cleansing cream, skin milk, emollient lotion, massage cream, emollient cream, make-up base, lipstick, facial pack or facial gel, cleaner formulation (e.g., shampoos, rinses, body cleanser, hair-tonics, soaps, etc.), and/or dermatological composition (e.g., lotions, ointments, gels, creams, patches, sprays, etc.).

Thus, the present invention provides systems and compositions for the delivery (e.g., transdermal delivery) of nucleic acid (e.g., polynucleotides and/or nucleic acid residues, such as nucleotides and/or nucleosides). Among the many advantages of this invention is the ability to deliver nucleic acids (e.g., polynucleotides and/or nucleic acid residues) without injection and further without a requirement for mechanical or chemical abrasion or alteration of skin. Additional advantages include an ability to utilize unmodified nucleic acids thereby simplifying and reducing the cost of production of cosmetic and/or pharmaceutical preparations and, further, preserving (or potentially enhancing) biological activity of the nucleic acid.

Definitions

Abrasion: The term "abrasion," as used herein, refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g., magnesium or aluminum particles), acids (e.g., alpha-hydroxy acids or beta-hydroxy acids), and/or alcohols may cause abrasion. In general, permeation enhancers such as those described, for example, by Donovan (see, e.g., U.S. Patent Publications 2004/009180 and 2005/175636, and PCT Publication WO 04/06954), and Graham (see, e.g., U.S. Pat. No. 6,939,852 and U.S. Patent Publication 2006/093624), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. Amino acids, including carboxy- and/or amino-terminal amino acids in peptides, can be modified by methylation, amidation, acetylation, and/or substitution with other chemical groups that can change the peptide's circulating half-life without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Biologically active agent: As used herein, the phrase "biologically active agent" refers to any substance that has activity in a biological system and/or organism. For instance, a substance that, when administered to an organism, has a biological effect on that organism, is considered to be biologically active. In particular embodiments, where a polynucleotide is biologically active, a portion of that polynucleotide that shares at least one biological activity of the polynucleotide is typically referred to as a "biologically active" portion.

Characteristic portion: As used herein, the phrase a "characteristic portion" of a substance, in the broadest sense, is one that shares some degree of sequence and/or structural identity and/or at least one functional characteristic with the relevant intact substance. For example, a "characteristic portion" of a polynucleotide is one that contains a continuous stretch of nucleic acid residues, or a collection of continuous stretches of nucleic acid residues, that together are characteristic of a polynucleotide. In some embodiments, each such continuous stretch generally will contain at least 2, at least 5, at least 10, at least 15, at least 20, or more nucleic acid residues. In general, a characteristic portion is one that, in addition to the sequence identity specified above, shares at least one functional characteristic with the relevant intact polynucleotide. In some embodiments, the characteristic portion may be biologically active.

Homology: As used herein, the term "homology" refers to the overall relatedness between polymeric molecules, e.g., between polynucleotide molecules (e.g., DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar.

Hydrophilic: As used herein, a "hydrophilic" substance is a substance that may be soluble in polar solvents. In some embodiments, a hydrophilic substance can transiently bond with polar solvents. In some embodiments, a hydrophilic substance transiently bonds with polar solvents through hydrogen bonding. In some embodiments, the polar solvent is water. In some embodiments, a hydrophilic substance may be ionic. In some embodiments, a hydrophilic substance may be non-ionic. In some embodiments, a hydrophilic substance may dissolve more readily in water, polar solvents, or hydrophilic solvents than in oil, non-polar solvents, or hydrophobic solvents. In some embodiments, a hydrophilic substance may dissolve less readily in oil, non-polar solvents, or hydrophobic solvents than in water, polar solvents, or hydrophilic solvents. In some embodiments, a substance is hydrophilic relative to another substance because it is more soluble in water, polar solvents, or hydrophilic solvents than is the other substance. In some embodiments, a substance is hydrophilic relative to another substance because it is less soluble in oil, non-polar solvents, or hydrophobic solvents than is the other substance.

Hydrophobic: As used herein, a "hydrophobic" substance is a substance that may be soluble in non-polar solvents. In some embodiments, a hydrophobic substance is repelled from polar solvents. In some embodiments, the polar solvent is water. In some embodiments, hydrophobic substances are non-polar. In some embodiments, a hydrophobic substance may dissolve more readily in oil, non-polar solvents, or hydrophobic solvents than in water, polar solvents, or hydrophilic solvents. In some embodiments, a hydrophobic substance may dissolve less readily in water, polar solvents, or hydrophilic solvents than in oil, non-polar solvents, or hydrophobic solvents. In some embodiments, a substance is hydrophobic relative to another substance because it is more soluble in oil, non-polar solvents, or hydrophobic solvents than is the other substance. In some embodiments, a substance is hydrophobic relative to another substance because it is less soluble in water, polar solvents, or hydrophilic solvents than is the other substance.

Identity: As used herein, the term "identity" refers to the overall relatedness between polymeric molecules, e.g., between polynucleotide molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

In conjunction with: As used herein, the phrase "delivered in conjunction with" refers to the co-delivery of two or more substances or agents. In particular, according to the present invention, the phrase is used herein in reference to delivery of a biologically active agent with nanoparticles and/or nanoparticle compositions in accordance with the invention. A substance or agent is delivered in conjunction with nanoparticles when the substance or agent is combined with nanoparticles and/or nanoparticle compositions; is encapsulated or completely surrounded by nanoparticles; is embedded within an nanoparticle micellar membrane; and/or is associated with the outer surface of an nanoparticle micellar membrane. A substance or agent to be delivered in conjunction with nanoparticles and/or nanoparticle compositions may or may not be covalently linked to the nanoparticles and/or nanoparticle compositions. A substance or agent to be delivered in conjunction with nanoparticles and/or nanoparticle compositions may or may not be attached to the nanoparticles and/or nanoparticle compositions by adsorption forces.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than 90%, 91%, 92%, 93%, 94%, 95%, 96%, 97%, 98%, or 99% pure.

Microfluidized: As used herein, the term "microfluidized" means exposed to high shear forces. In some embodiments, such exposure to high shear forces is accomplished by exposure to high pressure; in some embodiments such high pressure is within the range of about 15,000 psi to about 26,000 psi. In some embodiments, such exposure to high shear forces is accomplished by cavitation. In some embodiments, such exposure to high shear forces is accomplished by passing a sample through an instrument such as, for example, a Microfluidizer® (Microfluidics Corporation/MFIC Corporation) or other like device that may be useful in creating a uniform nanoparticle composition. In some embodiments of the present invention, a sample is microfluidized through exposure to high shear forces for a period of time less than about 10 minutes. In some embodiments, the period of time is less than about 9, about 8, about 7, about 6, about 5, about 4, about 3, about 2, or about 1 minute(s). In some embodiments, the period of time is within the range of about 1-about 2 minutes. In some embodiments, the period of time is about 30 seconds. In some embodiments, a sample is "microfluidized" through a single exposure to high shear forces; such embodiments are referred to as "single pass" microfluidization.

Nanoparticle: As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane. A "micellar membrane" comprises amphiphilic entities which have aggregated to surround and enclose a space or compartment (e.g., to define a lumen).

Nanoparticle composition: As used herein, the term "nanoparticle composition" refers to any substance that contains at least one nanoparticle. In some embodiments, a nanoparticle composition is a uniform collection of nanoparticles. In some embodiments, nanoparticle compositions are dispersions or emulsions. In general, a dispersion or emulsion is formed when at least two immiscible materials are combined. An "oil-in-water" dispersion is one in which oily particles (or hydrophobic or non-polar) are dispersed within an aqueous dispersion medium. A "water-in-oil" dispersion is one in which aqueous (or hydrophilic or polar) particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. In some embodiments, nanoparticle compositions are nanoemulsions. In some embodiments, nanoparticle compositions comprise micelles. In some particular embodiments, a nanoparticle composition comprises amphiphilic entity nanoparticles as described in co-pending PCT application serial number PCT/US07/86018, entitled "Amphiphilic Entity Nanoparticles" and filed on Nov. 30, 2007. In some particular embodiments, a nanoparticle composition comprises a nanoemulsion as described in co-pending U.S. patent application Ser. No. 11/607,436, entitled "Botulinum Nanoemulsions" and filed on Dec. 1, 2006. In some embodiments, a nanoparticle composition is stable. In some embodiments, a nanoparticle composition includes one or more biologically active agents to be delivered in conjunction with the nanoparticles.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, e.g., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery (e.g., transdermal delivery).

Nutraceutical: As used herein, the term "nutraceutical" refers to any substance thought to provide medical, health, or biological benefits. In some embodiments, nutraceuticals may prevent disease. In some embodiments, nutraceuticals may provide basic nutritional value. In some embodiments, a nutraceutical is a food or part of a food. In some embodiments, a nutraceutical agent may be a class of isolated nutrients, dietary supplements, vitamins, minerals, herbs, fortified foods, healing foods, genetically engineered foods, and processed foods. Nutraceuticals may also be known as "phytochemical foods" or "functional foods."

Patient: As used herein, the term "patient" or "subject" refers to any organism to which a composition in accordance with the invention may be administered, e.g., for experimental, diagnostic, prophylactic, and/or therapeutic purposes. Typical patients include animals (e.g., mammals such as mice, rats, rabbits, non-human primates, and humans). In some embodiments, a patient is a human.

Premix: As used herein, the term "premix" refers to any combination of components that is subsequently used to generate a nanoparticle composition according to the present invention. For example, a premix is any collection of ingredients that, when subjected to high shear forces, generates nanoparticles according to the present invention. In some embodiments, a premix contains two or more immiscible solvents. In some embodiments, a premix contains components that self-assemble into nanoparticles. In some embodiments, a premix contains components that self-assemble into micelles. In some embodiments, a premix contains one or more amphiphilic entities as described in co-pending PCT application serial number PCT/US07/86018, entitled "Amphiphilic Entity Nanoparticles" and filed on Nov. 30, 2007. In some embodiments, a premix contains one or more nucleic acids (e.g., polynucleotides and/or nucleic acid residues, such as nucleotides and/or nucleosides); in some embodiments, a premix contains at least one other biologically active agent. In some embodiments, a premix is agitated, mixed, and/or stirred; in some embodiments, a premix is agitated, mixed, and/or stirred prior to being subjected to high shear force. In some embodiments, a premix comprises at least one solubilized component (i.e., at least one component that is in solution); in some such embodiments, the premix is subjected to high shear force after such solubilization is achieved.

Pure: As used herein, a substance and/or entity is "pure" if it is substantially free of other components. For example, a preparation that contains more than about 90% of a particular substance and/or entity is typically considered to be a pure preparation. In some embodiments, a substance and/or entity is at least 91%, 92%, 93%, 94%, 95%, 96%, 97%, 98%, or 99% pure.

Shear force: As used herein, the term "shear force" refers to a force that is parallel to the face of a material, as opposed to a force that is perpendicular to the face of a material. In some embodiments, a composition exposed to high shear forces in order to produce a uniform nanoparticle composition. Any method known in the art can be used to generate high shear forces. In some embodiments, cavitation is used to generate high shear forces. In some embodiments, high pressure homogenization is used to generate high shear forces. Alternatively or additionally, high shear force may be administered by exposure to high pressure, for example about 15,000 psi. In some embodiments, such high pressure is within the range of about 18,000 psi to about 26,000 psi; in some embodiments, it is within the range of about 20,000 psi to about 25,000 psi. In some embodiments, a Microfluidizer® Processor (Microfluidics Corporation/MFIC Corporation) or other like device is used to generate high shear force. Microfluidizer® Processors provide high pressure and a resultant high shear rate by accelerating a composition through microchannels (typically having dimensions on the order of 75 microns) at a high velocity (typically in the range of 50 m/s-300 m/s) for size reduction to the nanoscale range. As the fluid exits the microchannels it forms jets which collide with jets from opposing microchannels. In the channels the fluid experiences high shear (up to $10^7$ l/s) which is orders of magnitude higher than that of conventional technologies. Jet collisions result in mixing in submicron level. Therefore, in such devices, high shear and/or impact can achieve particle size reduction and mixing of multiphase. In some embodiments of the present invention, a sample is exposed to high shear forces for a period of time less than about 10 minutes. In some embodiments, the period of time is less than about 9 minutes, about 8 minutes, about 7 minutes, about 6 minutes, about 5 minutes, about 4 minutes, about 3 minutes, about 2 minutes, or about 1 minute. In some embodiments, the period of time is within the range of about 1 minute-about 2 minutes; in some embodiments, the period of time is less than about 1 minute; in some embodiments, the period of time is about 30 seconds. In some embodiments, a sample is "microfluidized" through a single exposure to high shear forces; such embodiments are referred to herein as "single pass" microfluidization.

Similarity: As used herein, the term "similarity" refers to the overall relatedness between polymeric molecules, e.g., between polynucleotide molecules (e.g., DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small Molecule: In general, a "small molecule" is an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Typically, in accordance with the present invention, small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule. As one example, a pro-drug of a small molecule is a derivative of that small molecule. An analog of a small molecule refers to a molecule that shares the same or similar structural core as the original small molecule, and which is synthesized by a similar or related route, or art-recognized variation, as the original small molecule.

Stable: The term "stable," when applied to nanoparticle compositions herein, means that the compositions maintain one or more aspects of their physical structure (e.g., size range and/or distribution of particles) over a period of time. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, 10 hours, one (1) day, one (1) week, two (2) weeks, one (1) month, two (2) months, three (3) months, four (4) months, five (5) months, six (6) months, eight (8) months, ten (10) months, twelve (12) months, twenty-four (24) months, or longer. In some embodiments, the period of time is within the range of about one (1) day to twenty-four (24) months, two (2) weeks to twelve (12) months, two (2) months to five (5) months, etc. For example, if a nanoparticle composition is subjected to prolonged storage, temperature changes, and/or pH changes and a majority of the nanoparticles in the composition maintain a diameter within a stated range (for example, between approximately 10 nm-120 nm), the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9% or more. In some embodiments, where a nanoparticle composition comprises at least one biologically active agent, the nanoparticle composition is considered stable if the concentration of biologically active agent (e.g., nucleic acid) is maintained in the composition over the designated period of time under a designated set of conditions.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially free of: A nanoparticle composition is said to be "substantially free of" particles whose diameter is outside of a stated range when no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Suffering from: An individual who is "suffering from" a disease, disorder, or condition (e.g., wounds, abnormal skin cell proliferation, tissue connective diseases such as scleroderma, pachyonychia congenita, skin inflammation, psoriasis, sunburn or other types of skin damage, skin cancer, etc.) has been diagnosed with or exhibits symptoms of the disease, disorder, or condition.

Therapeutically effective amount: As used herein, the term "therapeutically effective amount" means an amount of nanoparticle composition that is sufficient, when administered to a patient suffering from or susceptible to a disease, disorder, and/or condition, to treat the disease, disorder, and/or condition.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relives, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Toxic solvent: As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl foramide, chloroform, tetramethyl foramide, acetone, acetates, and alkanes.

Uniform: The term "uniform," when used herein in reference to a nanoparticle composition, refers to a nanoparticle composition in which the individual nanoparticles have a specified range of particle diameter sizes. For example, in some embodiments, a uniform nanoparticle composition is one in which the difference between the minimum diameter and maximum diameter does not exceed about 600 nm, about 550 nm, about 500 nm, about 450 nm, about 400 nm, about 350 nm, about 300 nm, about 250 nm, about 200 nm, about 150 nm, about 100 nm, about 90 nm, about 80 nm, about 70 nm, about 60 nm, about 50 nm, or fewer nm. In some embodiments, particles (e.g., nucleic acid-containing particles) within uniform nanoparticle compositions in accordance with the invention have diameters that are smaller than about 600 nm, about 550 nm, about 500 nm, about 450 nm, about 400 nm, about 350 nm, about 300 nm, about 250 nm, about 200 nm, about 150 nm, about 130 nm, about 120 nm, about 115 nm, about 110 nm, about 100 nm, about 90 nm, about 80 nm, or less. In some embodiments, particles (e.g., nucleic acid-containing particles) within uniform nanoparticle compositions in accordance with the invention have diameters within the range of about 10 and about 600 nanometers. In some embodiments, particles (e.g., nucleic acid-containing particles) within uniform nanoparticle compositions in accordance with the invention have diameters within the range of about 10 nm-about 300 nm, about 10 nm-about 200 nm, about 10 nm-about 150 nm, about 10 nm-about 130 nm, about 10 nm-about 120 nm, about 10 nm-about 115 nm, about 10 nm-about 110 nm, about 10 nm-about 100 nm, or about 10 nm-about 90 nm. In some embodiments, particles (e.g., nucleic acid-containing particles) within nanoparticle compositions in accordance with the invention have an average particle size that is under about 300 nm, about 250 nm, about 200 nm, about 150 nm, about 130 nm, about 120 nm, about 115 nm, about 110 nm, about 100 nm, or about 90 nm. In some embodiments, the average particle size is within the range of about 10 nm-about 300 nm, about 50 nm-about 250 nm, about 60 nm-about 200 nm, about 65 nm-about 150 nm, about 70 nm-about 130 nm. In some embodiments, the average particle size is about 80 nm-about 110 nm. In some embodiments, the average particle size is about 90 nm-about 100 nm. In some embodiments, a majority of the particles (e.g., nucleic acid-containing particles) within uniform nanoparticle compositions in accordance with the invention have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition. In some embodiments, a uniform nanoparticle composition is achieved by microfluidization of a sample. In some embodiments, a uniform nanoparticle composition is prepared by exposure to high shear force, e.g., by microfluidization.

Unmodified nucleic acid: As used herein, the term "unmodified nucleic acid" refers to a nucleic acid (e.g., polynucleotide, nucleotide, nucleoside, etc.) that has not been chemically modified through the addition of other covalently-bonded functional groups intended to achieve delivery (e.g., transdermal delivery) of the polynucleotide, nucleotide, and/or nucleoside. In some embodiments, the nucleic acid has not been modified to add a phosphate group. In some embodiments, the nucleic acid has not been chemically modified to add any functional phosphate groups.

DESCRIPTION OF CERTAIN EMBODIMENTS

Nanoparticles

As discussed herein, the present invention describes nanoparticle compositions. In some embodiments, nanoparticle compositions incorporate one or more unmodified or modified nucleic acids (e.g., polynucleotides and/or nucleic acid residues, such as nucleotides and/or nucleosides). In some embodiments, such nanoparticle compositions further include one or more other biologically active agents in addition to nucleic acids. In some embodiments, nanoparticle compositions are formulated with one or more other components, for example in a pharmaceutical or cosmetic preparation. In some embodiments, such a pharmaceutical or cosmetic preparation is formulated to achieve delivery (in particular, transdermal delivery) of nucleic acids (and/or one or more other biologically active agents). In some embodiments, such a pharmaceutical or cosmetic preparation is formulated to achieve delivery (in particular, transdermal delivery) of nucleic acids which have been selected for their activity at the site of biological action. In some embodiments, the nucleic acids have been modified to enhance their activity at the site of biological action.

In some embodiments, nanoparticle compositions comprise a population of nanoparticles. In some embodiments, nanoparticles incorporate one or more unmodified or modified nucleic acids (e.g., polynucleotides and/or nucleic acid residues, such as nucleotides and/or nucleosides). In some embodiments, such nanoparticles further include one or more other biologically active agents in addition to nucleic acids.

Characteristics of Nanoparticles

In some embodiments, nanoparticle compositions in accordance with the invention are stable. In some embodiments, nanoparticle compositions in accordance with the invention are uniform.

In some embodiments, a uniform nanoparticle composition comprises a population of particles whose difference between the minimum and maximum diameters does not exceed approximately 600 nm, approximately 550 nm, approximately 500 nm, approximately 450 nm, approximately 400 nm, approximately 350 nm, approximately 300 nm, approximately 250 nm, approximately 200 nm, approximately 150 nm, or approximately 100 nm.

In some embodiments, nanoparticles in accordance with the invention have diameters that are smaller than about 1000 nm, about 600 nm, about 550 nm, about 500 nm, about 450 nm, about 400 nm, about 350 nm, about 300 nm, about 250 nm, about 200 nm, about 150 nm, about 130 nm, about 120 nm, about 115 nm, about 110 run, about 100 nm, about 90 nm, about 80 nm, about 50 nm, or less.

In some embodiments, nanoparticles in accordance with the invention have a diameter of 1 nm to 1000 nm, 1 nm to 600 nm, 1 nm to 500 nm, 1 nm to 400 nm, 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, nanoparticle compositions have a diameter of 1 nm to 15 nm, 15 nm to 200 nm, 25 nm to 200 nm, 50 nm to 200 nm, or 75 nm to 200 nm.

In some embodiments, the total particle distribution is encompassed within the specified range of particle diameter size. In some embodiments, less than 50%, 25%, 10%, 5%, or 1% of the total particle distribution is outside of the specified range of particle diameter sizes. In some embodiments, less than 1% of the total particle distribution is outside of the specified range of particle diameter sizes. In certain embodiments, the nanoparticle composition is substantially free of particles having a diameter larger than 300 nm, 250 nm, 200 nm, 150 nm, 120 nm, 100 nm, 75 nm, 50 nm, or 25 nm.

In some embodiments, nanoparticles within nanoparticle compositions have an average particle size that is under about 300 nm, about 250 nm, about 200 nm, about 150 nm, about 130 nm, about 120 nm, about 115 nm, about 110 nm, about 100 nm, about 90 nm, or about 50 nm. In some embodiments, the average particle size is within the range of about 10 nm-about 300 nm, about 50 nm-about 250, about 60 nm-about 200 nm, about 65 nm-about 150 nm, or about 70 nm-about 130 nm. In some embodiments, the average particle size is about 80 nm-about 110 nm. In some embodiments, the average particle size is about 90 nm-about 100 nm.

In some embodiments, nanoparticle compositions in accordance with the invention are substantially free of particles having a diameter in excess of 300 nm. Specifically, in some embodiments, fewer than 50%, of the nanoparticles in nanoparticle compositions in accordance with the invention have a diameter in excess of 300 nm. In some embodiments, fewer than 25% of the particles have a diameter in excess of 300 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 300 nm. Furthermore, in some embodiments, the nanoparticles in nanoparticle compositions have diameters within the range of 10 nm-300 nm.

In some embodiments, nanoparticle compositions in accordance with the invention are substantially free of particles having a diameter in excess of 200 nm. Specifically, in some embodiments, fewer than 50%, of the nanoparticles in nanoparticle compositions have a diameter in excess of 200 nm. In some embodiments, fewer than 25% of the particles have a diameter in excess of 200 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 200 nm. Furthermore, in some embodiments, the nanoparticles in nanoparticle compositions have diameters within the range of 10 nm-200 nm.

In some embodiments, nanoparticle compositions in accordance with the invention are substantially free of particles having a diameter in excess of 120 nm. Specifically, in some embodiments, fewer than 50%, of the nanoparticles in nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm.

In some embodiments, a majority of the nanoparticles within nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, a majority of nanoparticles in a nanoparticle composition have diameters between 10 nm and 120 nm. In some embodiments, a majority of nanoparticles in a nanoparticle composition have diameters between 20 nm and 120 nm. In some embodiments, a majority of nanoparticles in a nanoparticle composition have diameters between 20 nm and 110 nm. In some embodiments, a majority of nanoparticles in a nanoparticle composition have diameters between 20 nm and 100 nm. In some embodiments, a majority of nanoparticles in a nanoparticle composition have diameters between 20 nm and 90 nm. In some embodiments, a majority of nanoparticles in a nanoparticle composition have diameters between 20 nm and 80 nm. In some embodiments, a majority of nanoparticles in a nanoparticle composition have diameters between 20 nm and 70 nm. In some embodiments, a majority of nanoparticles in a nanoparticle composition have diameters between 20 nm and 60 nm. In some embodiments, a majority of nanoparticles in a nanoparticle composition have diameters between 20 nm and 50 nm. In some embodiments, a majority of nanoparticles in a nanoparticle composition have diameters between 20 nm and 40 nm. In some embodiments, a majority of nanoparticles in a nanoparticle composition have diameters between 20 nm and 30 nm.

In certain embodiments, about 50% of nanoparticles in a nanoparticle composition have diameters between 10 nm and 40 nm. In certain embodiments, about 90% of nanoparticles in a nanoparticle composition have diameters between 10 nm and 80 nm. In certain embodiments, about 90% of nanoparticles in a nanoparticle composition have diameters between 10 nm and 90 nm. In certain embodiments, about 95% of nanoparticles in a nanoparticle composition have diameters between 10 nm and 110 nm. In certain embodiments, about 95% of nanoparticles in a nanoparticle composition have diameters between 10 nm and 120 nm.

In certain embodiments, about 50% of the aggregate volume of all nanoparticles in a nanoparticle composition comprises or consists of nanoparticles having diameters between 10 nm and 40 nm. In certain embodiments, about 90% of the aggregate volume of all nanoparticles in a nanoparticle composition comprises or consists of nanoparticles having diameters between 10 nm and 80 nm. In certain embodiments, about 95% of the aggregate volume of all nanoparticles in a nanoparticle composition comprises or consists of nanoparticles having diameters between 10 nm and 110 nm. In certain embodiments, about 95% of the aggregate volume of all nanoparticles in a nanoparticle composition comprises or consists of nanoparticles having diameters between 10 nm and 120 nm.

Zeta potential is a measurement of the electric potential at a shear plane. A shear plane is an imaginary surface separating a thin layer of liquid bound to a solid surface (e.g., nanoparticle surface) and showing elastic behavior from the rest of liquid (e.g., liquid dispersion medium) showing normal viscous behavior. In some embodiments, nanoparticles have a zeta potential ranging between −80 mV and +80 mV. In some embodiments, nanoparticles have a zeta potential ranging between −50 mV and +50 mV. In some embodiments, nanoparticles have a zeta potential ranging between −25 mV and +25 mV. In some embodiments, nanoparticles have a zeta potential ranging between −10 mV and +10 mV. In some embodiments, nanoparticles have a zeta potential of about −80 mV, about −70 mV, about −60 mV, about −50 mV, about −40 mV, about −30 mV, about −25 mV, about −20 mV, about −15 mV, about −10 mV, or about −5 mV. In some embodiments, nanoparticles have a zeta potential of about +50 mV, about +40 mV, about +30 mV, about +25 mV, about +20 mV, about +15 mV, about +10 mV, or about +5 mV. In some embodiments, nanoparticles have a zeta potential that is about 0 mV.

In some embodiments, nanoparticles have a zeta potential that is about −5 mV to about −80 mV. In some embodiments, nanoparticles have a zeta potential that is about −5 mV to about −70 mV. In some embodiments, nanoparticles have a zeta potential that is about −5 mV to about −60 mV. In some embodiments, nanoparticles have a zeta potential that is about −5 mV to about −50 mV. In some embodiments, nanoparticles have a zeta potential that is about −5 mV to about −40 mV. In some embodiments, nanoparticles have a zeta potential that is about −5 mV to about −30 mV. In some embodiments, nanoparticles have a zeta potential that is about −5 mV to about −20 mV.

In some embodiments, nanoparticles have a zeta potential that is about −10 mV to about −15 mV. In some embodiments, nanoparticles have a zeta potential that is about −10 mV to about −80 mV. In some embodiments, nanoparticles have a zeta potential that is about −10 mV to about −70 mV. In some embodiments, nanoparticles have a zeta potential that is about −10 mV to about −60 mV. In some embodiments, nanoparticles have a zeta potential that is about −10 mV to about −50 mV. In some embodiments, nanoparticles have a zeta potential that is about −10 mV to about −40 mV. In some embodiments, nanoparticles have a zeta potential that is about −10 mV to about −30 mV. In some embodiments, nanoparticles have a zeta potential that is about −10 mV to about −20 mV.

In some embodiments, nanoparticles have a zeta potential that is about −80 mV to about −70 mV. In some embodiments, nanoparticles have a zeta potential that is about −70 mV to about −60 mV. In some embodiments, nanoparticles have a zeta potential that is about −60 mV to about −50 mV. In some embodiments, nanoparticles have a zeta potential that is about −50 mV to about −40 mV. In some embodiments, nanoparticles have a zeta potential that is about −40 mV to about −30 mV. In some embodiments, nanoparticles have a zeta potential that is about −30 mV to about −20 mV. In some embodiments, nanoparticles have a zeta potential that is about −20 mV to about −10 mV. In some embodiments, nanoparticles have a zeta potential that is about −10 mV to about 0 mV.

In some embodiments, nanoparticles have a zeta potential that is about −15 mV to about −20 mV. In some embodiments, nanoparticles have a zeta potential that is about −5 mV, about −6 mV, about −7 mV, about −8 mV, about −9 mV, −10 mV, about −11 mV, about −12 mV, about −13 mV, about −14 mV, about −15 mV, about 16 mV, about −17 mV, about −18 mV, about −19 mV, or about −20 mV.

In some embodiments nanoparticle compositions in accordance with the invention are emulsions or dispersions. In general, an emulsion or dispersion is formed from at least two immiscible materials, one of which will constitute the dispersion medium (i.e., the liquid medium in which particles (e.g., nanoparticles), which constituted the "dispersed medium") are dispersed. An "oil-in-water" dispersion is one in which oily particles are dispersed within an aqueous dispersion medium. A "water-in-oil" dispersion is one in which aqueous particles are dispersed within an oily dispersion medium. Oil-in-water and water-in-oil dispersions are discussed in further detail below. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. For example, emulsions or dispersions can be prepared from immiscible sets of hydrophobic/hydrophilic materials; polar/nonpolar materials, etc., regardless of whether such materials are strictly speaking "aqueous" or "oily."

In some embodiments, nanoparticle compositions in accordance with the invention comprise micellar structures (e.g., the nanoparticles are micelles). In some embodiments, such micellar structures are crosslinked. In some embodiments, such micellar structures are not crosslinked.

Production of Nanoparticles

In some embodiments, nanoparticle compositions in accordance with the invention self-assemble from a collection of combined components. In some embodiments, nanoparticle compositions are prepared by subjecting a combination of components (i.e., a "premix") to high shear force. In some embodiments, high shear force is applied by high pressure, by cavitation, by homogenization, and/or by microfluidization. In some embodiments, combined nanoparticle-forming components are agitated, stirred, or otherwise mixed. In some such embodiments, the components are subjected to high shear force after having been mixed. In some specific embodiments, mixing may be performed for a period of time such as, for example, less than one hour or more than 5, 6, 7, 8, 9, 10, 11, 12, 13, 14, or 15 hours. In some embodiments, solubilization is achieved.

In some embodiments, production of nanoparticle compositions involves dialyzing a collection of components, for example to remove any organic solvent, and/or freeze-drying to produce a composition.

In some embodiments of the present invention that utilize a premix, it is to be understood that the premix components may assemble into particles before the application of high shear force. At least some of such particles may be microparticles or even nanoparticles. In some embodiments, a nanoparticle composition is prepared from a premix, wherein the premix is selected from the group comprising a suspension or a microemulsion. In some embodiments, however, particle structures do not form in the premix before application of high shear force.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear force.

In certain embodiments, the premix is prepared as a solution prior to application of high shear force. In particular, for nanoparticle compositions that include at least one biologically active agent (e.g., a nucleic acid), it is often desirable for the biologically active agent to be dissolved in the premix before the high shear force is applied. Thus, in many embodiments, the biologically active agent is soluble in at least one of the media (or in a combination of media utilized in the premix). In some embodiments, such dissolution requires heating; in other embodiments it does not.

Composition of Nanoparticles

In some embodiments, nanoparticle compositions are prepared from components including one or more aqueous, polar, or hydrophilic medium(a), one or more oily, nonpolar, or hydrophobic medium(a), one or more micelle components, one or more surfactants or emulsifiers, one or more biologically active agents and/or one or more release retarding agents, etc.

Those of ordinary skill in the art will be well aware of suitable aqueous media that can be used as dispersion media or as media to be dispersed in accordance with the present invention. Representative such aqueous media include, for example, water, saline solutions (including phosphate buffered saline), water for injection, short chain alcohols, 5% dextrose, Ringer's solutions (lactated Ringer's injection, lactated Ringer's plus 5% dextrose injection, acylated Ringer's injection), NORMOSOL® M, ISOLYTE E, and the like, and combinations thereof.

Those of ordinary skill in the art will also be well aware of suitable oily media that can be used as dispersion media or as media to be dispersed in accordance with the present invention. In some embodiments, the oil may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride. In some embodiments, the oil is a medium chain triglyceride. In general, medium chain triglycerides are fatty acids containing 6-12 carbons atoms (e.g., caprylic acid, octanoic acid, capric acid, decanoic acid, lauric acid, etc.) and may be obtained from coconut oil or palm kernel oil. In some embodiments 1349 oil is a medium-chain triglyceride that can be utilized in accordance with the invention.

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mineral, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, wheat germ, and mixtures thereof. Suitable synthetic oils for use with the present invention include, but are not limited to: caprylic/capric triglyceride, cyclomethicone, diethyl sebacate, dimethicone 360, isopropyl myristate, octyldodecanol, oleyl alcohol, 1349 oil, and combinations thereof.

Appropriate micelle components may include, for example, one or more amphiphilic entities. Useful amphiphilic entities include natural entities, synthetic entities, and entities that contain both natural and synthetic components. In some embodiments, amphiphilic entities may comprise one or more polymers, and/or one or more compounds with polymeric character.

In general, an amphiphilic entity is one that has both hydrophobic and hydrophilic natures. As will be appreciated by those of ordinary skill in the art, an amphiphilic entity can be comprised in any number of different ways. In some embodiments, an amphiphilic entity may comprise one or more individual compounds or molecules that are themselves amphiphilic. To give but a few examples, such compounds or molecules include polyethylene glycol (PEG), phospholipids, cholesterols, glycolipids fatty acids, bile acids, and saponins. PEG is generally recognized as safe for use in food, cosmetics, and medicines by the U.S. Food and Drug Administration. PEG is water-soluble, non-toxic, odorless, lubricating, nonvolatile, and nonirritating.

In some embodiments, an amphiphilic entity may comprise one or more individual components that are not themselves amphiphilic but that has some hydrophilic or hydrophobic character. In such embodiments, two or more such non-amphiphilic components will typically be associated with one another such that the assemblage of the individual components is amphiphilic. Such association may or may not involve covalent linkage; such association may involve non-covalent bonding (e.g., via hydrophobic interactions, hydrogen bonding, Van der Waals interactions, ionic interaction, dipole-dipole interaction, etc.). In general, such association may involve any relevant force, bond, or means of adhesion.

In some embodiments, an amphiphilic entity for use in accordance with the present invention may be constructed from two or more individual components having differing degrees of hydrophilicity or hydrophobicity. In certain embodiments, an amphiphilic entity may comprise at least one hydrophilic component and at least one hydrophobic component. In certain embodiments, the "hydrophilic" and "hydrophobic" components are either hydrophilic or hydrophobic relative to one another.

In some embodiments, two or more components of differing degrees of hydrophilicity or hydrophobicity may be bonded together by covalent bonds to form a homopolymer or a co-polymer. In some embodiments, a co-polymer may be a block co-polymer. In some embodiments, a co-polymer may be a graft co-polymer.

In some embodiments, an amphiphilic entity may comprise or consist of an amphiphilic block co-polymer. In some embodiments, an amphiphilic block co-polymer may be a diblock co-polymer. In certain embodiments, an amphiphilic diblock co-polymer may comprise a first polymer block and a second polymer block connected covalently at the chain ends. In specific embodiments, the first polymer block may comprise repeating units of a hydrophilic component, and the second polymer block may comprise repeating units of a hydrophobic component. In specific embodiments, the first polymer block may comprise repeating units of a hydrophobic component, and the second polymer block may comprise repeating units of a hydrophilic component. In some embodiments, an amphiphilic block co-polymer may be a multiblock co-polymer. In certain embodiments, an amphiphilic block co-polymer may comprise multiple alternating blocks of two or more polymers connected covalently at the chain ends. In specific embodiments, an amphiphilic block co-polymer may comprise multiple alternating hydrophilic blocks and hydrophobic blocks connected covalently at the chain ends. In specific embodiments, each block of the alternating blocks may comprise repeating units of either hydrophilic components or hydrophobic components.

In some embodiments, an amphiphilic entity may comprise or consist of an amphiphilic graft co-polymer. In some embodiments, an amphiphilic graft co-polymer may comprise or consist of blocks of polymers connected covalently to the side chains of other blocks of polymers. In specific embodiments, each polymer block may comprise or consist of repeating units of either hydrophilic or hydrophobic components. In certain embodiments, an amphiphilic graft co-polymer may comprise or consist of a first polymer block and a second polymer block connected covalently to a side chain of the first polymer block. In certain embodiments, the first polymer block may comprise or consist of repeating units of a hydrophilic component, and the second block may comprise repeating units of a hydrophobic component. In certain embodiments, the first polymer block may comprise or consist of repeating units of a hydrophobic component, and the second block may comprise repeating units of a hydrophilic component.

In some embodiments, an amphiphilic block or graft co-polymer may include a hydrophilic polymer block comprising repeating units of a polysaccharide and a hydrophobic polymer block comprising repeating units of a polyester or polysaccharide. Alternatively or additionally, an amphiphilic block or graft co-polymer may include a hydrophobic polymer block comprising repeating units of a polysaccharide and a hydrophilic polymer block comprising repeating units of a polyester or polysaccharide. Such a hydrophilic polymer block can contain repeating units of any type of hydrophilic polymer, such as a polysaccharide (e.g., pullulan) or polyalkene oxide (e.g., polyethylene oxide). The hydrophobic polymer block can contain repeating units of any type of hydrophobic polymer, such as a polycaprolactone or polyamide (e.g., polycaprolactam).

In some embodiments, the hydrophilic portion of the amphiphilic entity may be non-ionic. In some embodiments, the hydrophilic component of an amphiphilic entity comprises one or more ionic groups. In general, such ionic groups are hydrophilic and can confer hydrophilic nature on the amphiphilic entity.

In some embodiments, the ionic group may be cationic. In some embodiments, the cationic group may be an ammonium ($NH_4^+$), nitronium ($NO_2^+$), nitrosyl ($NO^+$), hydronium ($H_3O^+$), mercurous ($Hg_2^{2+}$), phosphonium ($PH_4^+$), vanadyl ($VO^{2+}$), or salt thereof.

In some embodiments, the ionic group may be anionic. In some embodiments, the anionic group may be a fatty acid, arsenide ($As^{3-}$), azide ($N_3^-$), bromide ($Br^-$), chloride ($Cl^-$), fluoride ($F^-$), hydride ($H^-$), iodide ($I^-$), nitride ($N^{3-}$), oxide ($O^{2-}$), phosphide ($P^{3-}$), selenide ($Se^{2-}$), sulfide ($S^{2-}$), peroxide ($O_2^{2-}$), arsenate ($AsO_4^{3-}$), arsenite ($AsO_3^{3-}$), borate ($BO_3^{3-}$), perbromate ($BrO_4^-$), bromate ($BrO_3^-$), bromite ($BrO_2^-$), hypobromite ($BrO^-$), carbonate ($CO_3^{2-}$), hydrogen carbonate ($HCO_3^-$), chlorate ($ClO_3^-$), perchlorate ($ClO_4^-$), chlorite ($ClO_2^-$), hypochlorite ($ClO^-$), chromate ($CrO_4^{2-}$), dichromate ($Cr_2O_7^{2-}$), perfluorate ($BrO_4^-$), fluorate ($BrO_3^-$), fluorite ($BrO_2^-$), hypofluorite ($BrO^-$), periodate ($IO_4^-$), iodate ($IO_3^-$), iodite ($IO_2^-$), hypoiodite ($IO^-$), nitrate ($NO_3^-$), nitrite ($NO_2^-$), phosphate ($PO_4^{3-}$), hydrogen phosphate ($HPO_4^{2-}$), dihydrogen phosphate ($H_2PO_4^-$), phosphite ($PO_3^{3-}$), silicate ($SiO_3^{2-}$), sulfate ($SO_4^{2-}$), thiosulfate ($S_2O_3^{2-}$), hydrogen sulfate ($HSO_4^-$), sulfite ($SO_3^{2-}$), hydrogen sulfite ($HSO_3^-$), sulfonate ($—S(=O)_2—O^-$), acetate ($C_2H_3O_2{}_-$), formate ($HCO_2^-$), oxalate ($C_2O_4^{2-}$), hydrogen oxalate ($HC_2O_4^-$), citrate ($C_6H_5O_7^{3-}$), succinate ($C_4H_4O_4^{2-}$), fumarate ($C_4H_2O_4^{2-}$), malate ($C_4H_5O_5^{2-}$), hydrogen sulfide ($HS^-$), telluride ($Te^{2-}$), amide ($NH_2^-$), cyanate ($OCN^-$), thiocyanate ($SCN^-$), cyanide ($CN^-$), hydroxide ($OH^-$), permanganate ($MnO_4^-$), or salt thereof.

In some embodiments, the hydrophilic component of an amphiphilic entity may comprise or consist of a nucleic acid. For example, a nucleic acid may include DNA, RNA, or combinations thereof. In some embodiments, a nucleic acid may be an oligonucleotide and/or polynucleotide. In some embodiments, a nucleic acid may be an oligonucleotide and/or modified oligonucleotide; RNAi-inducing agents; small interfering RNAs (siRNAs), short hairpin RNAs (shRNAs), and/or microRNAs (miRNAs); an antisense oligonucleotide and/or modified antisense oligonucleotide; a cDNA; a genomic DNA; viral DNA and/or RNA; DNA and/or RNA chimeras; plasmids; cosmids; gene fragments; an artificial and/or natural chromosome (e.g., a yeast artificial chromosome) and/or a part thereof; an RNA (e.g., an mRNA, a tRNA, an rRNA, and/or a ribozyme); a peptide nucleic acid (PNA); a polynucleotide comprising synthetic analogues of nucleic acids, which may be modified or unmodified; various structural forms of DNA including single-stranded DNA, double-stranded DNA, supercoiled DNA and/or triple-helical DNA; Z-DNA; and/or combinations thereof.

In some embodiments, the hydrophilic component of an amphiphilic entity may comprise or consist of a carbohydrate. In some embodiments, the carbohydrate may be a polysaccharide composed of simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, the polymer may be a hydrophilic carbohydrate, including aminated, carboxylated, and sulfated polysaccharides. In some embodiments, the hydrophilic carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

In some embodiments, the hydrophilic component of an amphiphilic entity may comprise or consist of a gum including, but not limited to, xanthan gum, alginic acid, caraya gum, sodium alginate, and/or locust bean gum.

In some embodiments, a component of an amphiphilic entity may comprise or consist of a protein. In some embodiments, a protein is a hydrophilic component of an amphiphilic entity. In other embodiments, a protein is a hydrophobic component of an amphiphilic entity. Exemplary proteins that may be used in accordance with the present invention include, but are not limited to, albumin, collagen, or a poly(amino acid) (e.g., polylysine).

In some embodiments, the hydrophobic component of an amphiphilic entity may comprise or consist of one or more fatty acid groups or salts thereof. In general, such groups are typically hydrophobic and can confer hydrophobic nature onto the amphiphilic entity. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, the hydrophobic component of an amphiphilic entity may comprise or consist of one or more biocompatible and/or biodegradable synthetic polymers, including, for example, polycarbonates (e.g., poly(1,3-dioxan-2one)), polyanhydrides (e.g., poly(sebacic anhydride)), polyhydroxyacids (e.g., poly((β-hydroxyalkanoate)), polypropylfumarates, polycaprolactones, polyamides (e.g., polycaprolactam), polyacetals, polyethers, polyesters (e.g., polylactide and polyglycolide), biodegradable polycyanoacrylates, polyvinyl alcohols, and biodegradable polyurethanes. For example, the amphiphilic entity may comprise one or more of the following biodegradable polymers: poly(lactic acid), poly(glycolic acid), poly(caprolactone), poly(lactide-co-glycolide), poly(lactide-co-caprolactone), poly(glycolide-co-caprolactone), and poly(D,L-lactide-co-glycolide).

In some embodiments, the hydrophobic component of an amphiphilic entity may comprise or consist of one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully-polymerized copolymers of acrylic and methacrylic acid esters with a low content of quaternary ammonium groups.

In some embodiments, the hydrophobic component of an amphiphilic entity may comprise or consist of a polyester. Exemplary such polyesters include, for example, polyalkylene glycols, poly(glycolide-co-lactide), poly(lactic-co-glycolic acid)-PEG copolymers, poly(lactic acid), poly(lactic acid)-PEG copolymers, poly(glycolic acid), poly(glycolic acid)-PEG copolymers, co-polymers of polylactic and polyglycolic acid, and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly(ethylene imine)-PEG copolymers, and derivatives thereof. In some embodiments, polyesters may include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

Suitable surfactants or emulsifying agents include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (SPAN® 85) glycocholate; sorbitan monolaurate (SPAN® 20); polysorbate 20 (TWEEN® 20); polysorbate 60 (TWEEN® 60); polysorbate 65 (TWEEN® 65); polysorbate 80 (TWEEN® 80); polysorbate 85 (TWEEN® 85); polyoxyethylene monostearate; surfactin; a poloxomer; a sorbitan fatty acid ester such as sorbitan trioleate; lecithin; soybean lecithin; lysolecithin; lipoid; phosphatidylserine; phosphatidylinositol; sphingomyelin; phosphatidylethanolamine(cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; tyloxapol; poly(ethylene glycol)5000-phosphatidylethanolamine; poly(ethylene glycol) 400-monostearate; and phospholipids. The surfactant component may be a mixture of different surfactants. These surfactants may be extracted and purified from a natural source or may be prepared synthetically in a laboratory. In a preferred embodiment, the surfactants are commercially available.

In certain embodiments, relative amounts of components utilized to prepare nanoparticle compositions are selected or adjusted to generate nanoparticles having desired characteristics. In some embodiments, nanoparticle compositions (e.g., comprising nanoparticles that incorporate unmodified and/or modified polynucleotides) comprise surfactant, oil, and/or aqueous medium (e.g., water) in specified ratios. In some embodiments, the oil and surfactant are utilized at a ratio ranging between 0.5-10. In some embodiments, the ratio of oil to surfactant is approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, the ratio of surfactant to oil is approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1.

In some embodiments, oil and surfactant are utilized at a ratio ranging between 0.5-2. In certain embodiments, the ratio of oil to surfactant is approximately 0.5:1, approximately 1:1, or approximately 2:1. In certain embodiments, the ratio of surfactant to oil is approximately 0.5:1, approximately 1:1, or approximately 2:1. In certain specific embodiments, the ratio of oil to surfactant is approximately 1:1.

In some embodiments, compositions utilizing such ratios of oil to surfactant comprise oil-in-water emulsions. In some embodiments, compositions utilizing such ratios of oil to surfactant comprise nanoparticles that incorporate unmodified and/or modified polynucleotides.

In some embodiments, the water and surfactant are utilized at a ratio ranging between 0.5-10. In some embodiments, the ratio of water to surfactant is approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, the ratio of surfactant to water is approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, water and surfactant are utilized at a ratio ranging between 0.5-2. In certain embodiments, the ratio of water to surfactant is approximately 0.5:1, approximately 1:1, or approximately 2:1. In certain embodiments, the ratio of surfactant to water is approximately 0.5:1, approximately 1:1, or approximately 2:1. In certain specific embodiments, the ratio of water to surfactant is approximately 1:1. In some embodiments, compositions utilizing such ratios of water to surfactant comprise water-in-oil emulsions.

In some embodiments, the percent of oil in the composition from which nanoparticles are prepared (e.g., in the premix) ranges between 0% and 30%. In some embodiments the percent of oil in the composition from which nanoparticles are prepared (e.g., in the premix) is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29% or approximately 30%. In some embodiments the percent of oil is approximately 9%. In some embodiments the percent of oil is approximately 5%.

The percent of water in the premix can range from 0% to 99%, from 10% to 99%, from 25% to 99%, from 50% to 99%, or from 75% to 99%. In some embodiments, the percent of water in the premix can range from 0% to 75%, from 0% to 50%, from 0% to 25%, or from 0% to 10%. In some embodiments, the percent of water in the composition from which nanoparticles are prepared (e.g., in the premix) ranges between 0% and 30%. In some embodiments the percent of water is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29% or approximately 30%. In some embodiments the percent of water is approximately 9%. In some embodiments the percent of water is approximately 5%.

In some embodiments, where one or more amphiphilic entities is/are utilized, the percent of amphiphilic entity in the composition from which nanoparticles are prepared (e.g., in the premix) can range from 40% to 99%, from 50% to 99%, from 60% to 99%, from 70% to 99%, from 80% to 99%, from 80% to 90%, or from 90% to 99%. In some embodiments the percent of amphiphilic entity in the composition from which nanoparticles are prepared (e.g., in the premix) is approximately 75%, approximately 76%, approximately 77%, approximately 78%, approximately 79%, approximately 80%, approximately 81%, approximately 82%, approximately 83%, approximately 84%, approximately 85%, approximately 86%, approximately 87%, approximately 88%, approximately 89%, approximately 90%, approximately 91%, approximately 92%, approximately 93%, approximately 94%, approximately 95%, approximately 96%, approximately 97%, approximately 98%, or approximately 99%.

The percent of substances with surfactant activity in the premix can range from 0% to 99%, from 10% to 99%, from 25% to 99%, from 50% to 99%, or from 75% to 99%. In some embodiments, the percent of substances with surfactant activity in the premix can range from 0% to 75%, from 0% to 50%, from 0% to 25%, or from 0% to 10%. In some embodiments, the percent of substances with surfactant activity in the composition from which nanoparticles are prepared (e.g., in the premix) ranges between 0% and 30%. In some embodiments the percent of substances with surfactant activity is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29% or approximately 30%. In some embodiments the percent of substances with surfactant activity is approximately 9%. In some embodiments the percent of substances with surfactant activity is approximately 5%.

In some embodiments, the nanoparticle composition does not contain more than one oil. In some embodiments, the nanoparticle composition may comprise two or more oils. In some embodiments, the nanoparticle composition does not contain more than one surfactant. In some embodiments, the nanoparticle composition may comprise two or more surfactants. In some embodiments, the nanoparticle composition is completely free or substantially free of toxic components.

In some embodiments, the nanoparticle composition consists essentially of water, an oil, a surfactant, and at least one biologically active agent (e.g., a nucleic acid). In some embodiments, the nanoparticle composition consists essentially of water, an oil, a surfactant, at least one biologically active agent, and at least one substance used to produce and/or preserve the nanoparticle composition.

In some embodiments, the nanoparticle composition consists of water, an oil, a surfactant, and a nucleic acid. In some embodiments, the nanoparticle composition consists of water, an oil, a surfactant, a nucleic acid, and at least one substance used to produce and/or preserve the nanoparticle.

by a glycosidic bond. In general, a nucleotide comprises a nucleoside and one to three 5' phosphate groups.

TABLE 1

Heterocyclic Nitrogenous Bases

| Trivial Name | Symbol | Systemic Name | Formula |
|---|---|---|---|
| Adenine (6-aminopurine) | A | 7H-purin-6-amine | 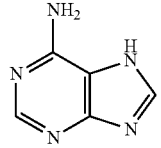 |
| Cytosine | C | 4-amino-3H-pyrimidin-2-one | 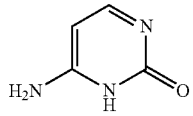 |
| Guanine (2-amino-6-oxo-purine; 2-aminohypoxanthine) | G | 2-amino-1H-purin-6(9H)-one | 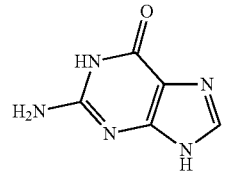 [SMILES: Nc1nc2[nH]cnc2c(=O)[nH]1] |
| Thymine (5-methyluracil) | T | 5-Methylpyrimidine-2,4(1H,3H)-dione | 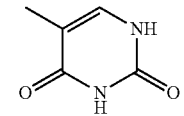 |
| Uracil (2-oxy-4-oxy pyrimidine; 2,4(1H,3H)-pyrimidinedione; 2,4-dihydroxypryimidine; 2,4-pyrimidinediol) | U | Pyrimidine-2,4(1H,3H)-dione | 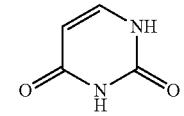 |

Nucleic Acids

Any of a variety of nucleic acids may be incorporated in nanoparticle compositions according to the present invention. In some embodiments, a nucleic acid to be incorporated in a nanoparticle composition is a polynucleotide. In some embodiments, a nucleic acid to be incorporated in a nanoparticle composition is a nucleotide. In some embodiments, a nucleic acid to be incorporated in a nanoparticle composition is a nucleoside.

In some embodiments, a nucleic acid is less than about 50 nucleotides in length. In some embodiments, a nucleic acid is less than about 90, about 80, about 70, about 65, about 60, about 55, about 50, about 45, about 40, about 35, about 30, about 25, about 20, about 15, about 13, about 12, about 10, about 9, about 8, about 7, about 6, about 5, about 4, about 3, or about 2 nucleotides in length. In some specific embodiments, a nucleic acid is a single nucleic acid residue (e.g., a single nucleotide or a single nucleoside). In some embodiments, a nucleic acid to be incorporated in a nanoparticle composition comprises only naturally-occurring nucleic acid residues (e.g., nucleotides, nucleosides). In some embodiments, a nucleic acid comprises one or more non-naturally occurring nucleic acid residues.

In general, a nucleoside comprises a pentose sugar (e.g., ribose or deoxyribose) and a heterocyclic nitrogenous base (e.g., purines: cytosine, thymidine, and uracil; and pyrimidines: guanine and adenine; see Table 1) covalently linked In some embodiments, a nucleic acid may be DNA, RNA, or combinations thereof. In some embodiments, the nucleic acid may be an oligonucleotide and/or polynucleotide. As used herein, the terms "oligonucleotide" and "polynucleotide" may be used interchangeably. In some embodiments, a nucleic acid may be an oligonucleotide and/or modified oligonucleotide (including, but not limited to, modifications through phosphorylation); an antisense oligonucleotide and/or modified antisense oligonucleotide (including, but not limited to, modifications through phosphorylation). In some embodiments, a nucleic acid may comprise cDNA and/or genomic DNA. In some embodiments, a nucleic acid may comprise non-human DNA and/or RNA (e.g., viral, bacterial, or fungal nucleic acid sequences). In some embodiments, a nucleic acid may be a plasmid, cosmid, gene fragment, artificial and/or natural chromosome (e.g., a yeast artificial chromosome), and/or a part thereof. In some embodiments, a nucleic acid may be a functional RNA (e.g., mRNA, a tRNA, an rRNA and/or a ribozyme). In some embodiments, a nucleic acid may be an RNAi-inducing agent, small interfering RNA (siRNA), short hairpin RNA (shRNA), and/or microRNA (miRNA). In some embodiments, a nucleic acid may be a peptide nucleic acid (PNA). In some embodiments, a nucleic acid may be a polynucleotide comprising synthetic analogues of nucleic acids, which may be modified or unmodified. In some embodiments, a nucleic acid may comprise various structural forms of DNA including single-stranded DNA, double-stranded DNA, supercoiled DNA and/or triple-helical DNA; Z-DNA; and/or combinations thereof.

Nucleic acids to be used in accordance with the present invention may be prepared according to any available technique including, but not limited to chemical synthesis, enzymatic synthesis, enzymatic or chemical cleavage of a longer precursor, etc. Methods of synthesizing nucleic acid polymers (e.g., polynucleotides) are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005).

Nucleic acids to be used in accordance with the present invention may comprise naturally-occurring nucleic acid residues. In some embodiments, naturally-occurring nucleic acid residues include nucleosides, modified nucleosides, naturally-occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleic acid residues or modified nucleic acid residues can be replaced with a hydrocarbon linker or a polyether linker provided that the binding affinity, selectivity, and/or other functional characteristics of the nucleic acid residues are not substantially reduced by the substitution.

It will be appreciated by those of ordinary skill in the art that nucleic acids in accordance with the present invention may comprise nucleic acid residues entirely of the types found in naturally occurring nucleic acids, or may instead include one or more nucleic acid residue analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleic acid residue analogs and modifications that may be used. See Crooke, S. (ed.) *Antisense Drug Technology: Principles, Strategies, and Applications* (1$^{st}$ ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, SR$_1$, NH$_2$, NH$_R$, NR$_2$ or CN, wherein R is C$_1$-C$_6$ alkyl, alkenyl, or alkynyl, and halo is F, Cl, Br, or I. Examples of modified linkages include phosphorothioate and 5'-N-phosphoramidite linkages.

Nucleic acids comprising a variety of different nucleic acid residue (e.g., nucleotide, nucleoside) analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleic acid residue monomers for the chemical synthesis of nucleic acids are readily available. In some cases, nucleic acids comprising residues having such modifications display improved properties relative to nucleic acids consisting only of naturally occurring residues. In some embodiments, nucleic acid modifications described herein are utilized to reduce and/or prevent digestion by nucleases (e.g., exonucleases, endonucleases, etc.). For example, the structure of a polynucleotide may be stabilized by including nucleotide analogs at the 3' end of one or both strands order to reduce digestion.

Modified nucleic acids (e.g., modified polynucleotides) need not be uniformly modified along the entire length of the polynucleotide. Different nucleic acid residue modifications and/or backbone structures may exist at various positions in the polynucleotide. One of ordinary skill in the art will appreciate that the residue analogs or other modification(s) may be located at any position(s) of a polynucleotide such that the function of the polynucleotide is not substantially affected. The modified region may be at the 5'-end and/or the 3'-end of one or both strands. For example, modified polynucleotides in which approximately 1 to approximately 5 residues at the 5' and/or 3' end of either of both strands are residue analogs and/or have a backbone modification have been employed. The modification may be a 5' or 3' terminal modification. One or both nucleic acid strands may comprise at least 50% unmodified residues, at least 80% unmodified residues, at least 90% unmodified residues, or 100% unmodified residues.

Nucleic acids in accordance with the present invention may, for example, comprise a modification to a sugar, residue, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art. In some embodiments, nucleic acids in accordance with the present invention may comprise one or more non-natural nucleoside linkages. In some embodiments, one or more internal nucleotides at the 3'-end, 5'-end, or both 3'- and 5'-ends of the nucleic acid are inverted to yield linkages such as a 3'-3' linkage or a 5'-5' linkage.

In some embodiments, nucleic acids in accordance with the present invention are not synthetic, but are naturally-occurring entities that have been isolated from their natural environments.

In certain specific embodiments, nucleic acids in accordance with the present invention comprise only naturally-occurring nucleic acid residues (e.g., nucleotides and/or nucleosides). In certain specific embodiments, nucleic acids in accordance with the present invention comprise only unmodified residues. The nanoparticle compositions of the present invention are capable of delivery (e.g., transdermal delivery) of both modified and unmodified nucleic acids.

Nucleic acids for use in accordance with the present invention, generally, are ones that have biological activity in the skin (e.g., epidermis and dermis), subcutaneous tissue (e.g., adipose tissue), contiguous muscles, and/or distant tissues (e.g., organs such as lungs, liver, etc.).

In some embodiments, a nucleic acid is or comprises a functional RNA (e.g., antisense oligonucleotide, ribozyme, RNA that participates in forming triple helical structures, etc.). In certain embodiments, a nucleic acid is or comprises an antisense molecule that binds to a translational start site, transcriptional start site, and/or splice junction. In some embodiments, antisense oligonucleotides prevent translation or post-transcriptional processing of RNA. Alternatively or additionally, antisense oligonucleotides may alter transcription of a target gene by binding to DNA of a target gene, such as, for example, a regulatory element.

Typically, antisense RNAs exhibit sufficient complementarity to a target transcript to allow hybridization of the antisense RNA to the target transcript. Mismatches are tolerated, as long as hybridization to the target can still occur. In general, antisense RNAs can be of any length, as long as hybridization can still occur. In some embodiments, antisense RNAs are about 20 nt, about 30 nt, about 40 nt, about 50 nt, about 75 nt, about 100 nt, about 150 nt, about 200 nt, about 250 nt, about 500 nt, or longer. In some embodiments, antisense RNAs comprise an inhibitory region that hybridizes with a target transcript of about 20 nt, about 30 nt, about 40 nt, about 50 nt, about 75 nt, about 100 nt, about 150 nt, about 200 nt, about 250 nt, about 500 nt, or longer.

In some embodiments, a nucleic acid is or comprises an agent that mediates RNA interference (RNAi). RNAi is a mechanism that inhibits expression of specific genes. RNAi typically inhibits gene expression at the level of translation, but can function by inhibiting gene expression at the level of transcription. RNAi targets include any RNA that might be present in cells, including but not limited to, cellular transcripts, pathogen transcripts (e.g., from viruses, bacteria, fungi, etc.), transposons, vectors, etc.

RNAi agents in accordance with the invention may target any portion of a transcript. In some embodiments, a target transcript is located within a coding sequence of a gene. In some embodiments, a target transcript is located within non-coding sequence. In some embodiments, a target transcript is located within an exon. In some embodiments, a target transcript is located within an intron. In some embodiments, a target transcript is located within a 5' untranslated region (UTR) or 3' UTR of a gene. In some embodiments, a target transcript is located within an enhancer region. In some embodiments, a target transcript is located within a promoter.

For any particular gene target, design of RNAi agents and/or RNAi-inducing agents typically follows certain guidelines. In general, it is desirable to avoid sections of target transcript that may be shared with other transcripts whose degradation is not desired. In some embodiments, RNAi agents and/or RNAi-inducing entities target transcripts and/or portions thereof that are highly conserved. In some embodiments, RNAi agents and/or RNAi-inducing entities target transcripts and/or portions thereof that are not highly conserved.

As used herein, a "small interfering RNA" or "siRNA" refers to an RNAi agent comprising an RNA duplex (referred to herein as a "duplex region") that is approximately 19 basepairs (bp) in length and optionally further comprises one or two single-stranded overhangs. In some embodiments, an siRNA comprises a duplex region ranging from 15 bp to 29 bp in length and optionally further comprising one or two single-stranded overhangs. An siRNA is typically formed from two RNA molecules (i.e., two strands) that hybridize together. One strand of an siRNA includes a portion that hybridizes with a target transcript. In some embodiments, siRNAs mediate inhibition of gene expression by causing degradation of target transcripts.

As used herein, a "short hairpin RNA" or "shRNA" refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop. In some embodiments, an shRNA comprises a duplex portion ranging from 15 bp to 29 bp in length and at least one single-stranded portion, typically ranging between approximately 1 nt and approximately 10 nt in length that forms a loop. In some embodiments, the single-stranded portion is approximately 1 nt, approximately 2 nt, approximately 3 nt, approximately 4 nt, approximately 5 nt, approximately 6 nt, approximately 7 nt, approximately 8 nt, approximately 9 nt, or approximately 10 nt in length. In some embodiments, shRNAs are processed into siRNAs by cellular RNAi machinery (e.g., by Dicer). Thus, in some embodiments, shRNAs may be precursors of siRNAs. Regardless, siRNAs in general are capable of inhibiting expression of a target RNA, similar to siRNAs. As used herein, the term "short RNAi agent" is used to refer to siRNAs and shRNAs, collectively.

Short RNAi agents typically include a base-paired region ("duplex region") between approximately 15 nt and approximately 29 nt long, e.g., approximately 19 nt long, and may optionally have one or more free or looped ends. RNAi-inducing agents and/or short RNAi agents typically include a region (the "duplex region"), one strand of which contains an inhibitory region between 15 nt to 29 nt in length that is sufficiently complementary to a portion of the target transcript (the "target portion"), so that a hybrid (the "core region") can form in vivo between this strand and the target transcript. The core region is understood not to include overhangs.

In some embodiments, siRNAs comprise 3' overhangs at one or both ends of the duplex region. In some embodiments, an shRNA comprises a 3' overhang at its free end. In some embodiments, siRNAs comprise a single nucleotide 3' overhang. In some embodiments, siRNAs comprise a 3' overhang of 2 nt. In some embodiments, siRNAs comprise a 3' overhang of 1 nt. Overhangs, if present, may, but need not be, complementary to the target transcript. siRNAs with 2 nt-3 nt overhangs on their 3' ends are frequently efficient in reducing target transcript levels than siRNAs with blunt ends.

In some embodiments, the inhibitory region of a short RNAi agent is 100% complementary to a region of a target transcript. However, in some embodiments, the inhibitory region of a short RNAi agent is less than 100% complementary to a region of a target transcript. The inhibitory region need only be sufficiently complementary to a target transcript such that hybridization can occur, e.g., under physiological conditions in a cell and/or in an in vitro system that supports RNAi (e.g., a *Drosophila* extract system).

One of ordinary skill in the art will appreciate that short RNAi agent duplexes may tolerate a mismatches and/or bulges, particularly mismatches within the central region of the duplex, while still leading to effective silencing. One of skill in the art will also recognize that it may be desirable to avoid mismatches in the central portion of the short RNAi agent/target transcript core region (see, e.g., Elbashir et al., *EMBO J.* 20:6877, 2001). For example, the 3' nucleotides of the antisense strand of the siRNA often do not contribute significantly to specificity of the target recognition and may be less critical for target cleavage.

micro RNAs (miRNAs) are genomically encoded non-coding RNAs of about 21-23 nucleotides in length that help regulate gene expression, particularly during development (see, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189; each of which are incorporated herein by reference). The phenomenon of RNA interference, broadly defined, includes the endogenously induced gene silencing effects of miRNAs as well as silencing triggered by foreign dsRNA. Mature miRNAs are structurally similar to siRNAs produced from exogenous dsRNA, but before reaching maturity, miRNAs first undergo extensive post-transcriptional modification. An miRNA is typically expressed from a much longer RNA-coding gene as a primary transcript known as a pri-miRNA, which is processed in the cell nucleus to a 70-nucleotide stem-loop structure called a pre-miRNA by the microprocessor complex. This complex consists of an RNase III enzyme called Drosha and a dsRNA-binding protein Pasha. The dsRNA portion of this pre-miRNA is bound and cleaved by dicer to produce the mature miRNA molecule that can be integrated into the RISC complex; thus, miRNA and siRNA share the same cellular machinery downstream of their initial processing (Gregory et al., 2006, *Meth. Mol. Biol.*, 342:33; incorporated herein by reference). In general, miRNAs are not perfectly complementary to their target transcripts.

In some embodiments, miRNAs can range between 18 nt-26 nt in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one or two single-stranded overhangs. In some embodiments, an RNAi agent comprises a duplex region ranging from 15 bp to 29 bp in length and optionally further comprising one to three single-stranded overhangs. An miRNA may be formed from two RNA molecules that hybridize together, or may alternatively be generated from a single RNA molecule that includes a self-hybridizing portion. The duplex portion of an miRNA usually, but does not necessarily, comprise one or more bulges consisting of one or more unpaired nucleotides. One strand of an miRNA includes a portion that hybridizes with a target RNA. In certain embodiments, one strand of the miRNA is not precisely complementary with a region of the target RNA, meaning that the miRNA hybridizes to the target RNA with one or more mismatches. In some embodiments, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

In certain embodiments, a nucleic acid is or comprises a ribozyme designed to catalytically cleave target mRNA transcripts may be used to prevent translation of a target mRNA and/or expression of a target (see, e.g., PCT publication WO 90/11364; and Sarver et al., 1990, *Science* 247:1222).

In certain embodiments, a nucleic acid is or comprises a nucleic acid that participates in forming triple helical structures. Endogenous target gene expression may be reduced by targeting deoxyribonucleotide sequences complementary to the regulatory region of the target gene (e.g., the target gene's promoter and/or enhancers) to form triple helical structures that prevent transcription of the target gene in target muscle cells in the body (see generally, Helene, 1991, *Anticancer Drug Des.* 6:569; Helene et al., 1992, *Ann, N.Y. Acad. Sci.* 660:27; and Maher, 1992, *Bioassays* 14:807).

In some instances, the mechanism by which a particular nucleic acid exerts a therapeutic effect and/or affects a biological activity is unknown. The present invention contemplates the use of such nucleic acids. In some embodiments, the methods of the present invention may be used for delivery (e.g., transdermal delivery) of biologically active nucleic acids (e.g., polynucleotides and/or nucleic acid residues) that have not yet been identified or characterized.

In some embodiments, nucleic acids to be used in accordance with the present invention improve wound healing. Such nucleic acids include DNA coding for keratinocyte growth factor-1 (KGF-1) (Lin et al., 2006, *Wound Repair Regen.*, 14:618). In some embodiments, nucleic acids coding for KGF-1 are characterized by all or a portion of a sequence as set forth in GenBank sequence NC_000015.

In some embodiments, nucleic acids to be used in accordance with the present invention may promote skin wound healing. Such nucleic acids include Connexin43 (Cx43) antisense oligonucleotides, RNAi agents, siRNAs, shRNAs, and/or miRNAs (Mori et al., 2006, *J. Cell Sci.*, 119:5193). In some embodiments, antisense oligonucleotides, RNAi agents, siRNAs, shRNAs, and/or miRNAs may target one or more regions and/or characteristic portions of a nucleic acid having a sequence such as that set forth in GenBank sequence AK312324.

In some embodiments, nucleic acids to be used in accordance with the present invention may suppress abnormal skin cell proliferation and enhance skin wound healing. Such nucleotides may include nucleotides and monophosphate nucleosides, diphosphate nucleosides, and triphosphate nucleosides. In some embodiments, such nucleic acids include adenine nucleotides and adenosine and adenosine triphosphate nucleosides (Brown et al., 2000, *J. Invest. Dermatol.*, 115:849; and Wang et al., 1990, *Biochem. Biophys. Res. Commun.*, 166:251).

In some embodiments, nucleic acids to be used in accordance with the present invention stimulate interferon production which inhibits collagen synthesis in the skin and has the potential to treat scleroderma, a tissue connective disease. Such nucleic acids include those that encode interferon gamma (IFNγ) (Badea et al., 2005, *J. Gene Med.*, 7:1200; and Gray and Goeddel, 1983, *Proc. Natl. Acad. Sci., USA,* 80:5842). In some embodiments, nucleic acids coding for IFNγ are characterized by all or a portion of a sequence as set forth in GenBank sequence NM_001127598, NM_000612, NM_001007139, or NC_000076.

In some embodiments, nucleic acids to be used in accordance with the present invention treat the skin disorder pachyonychia congenita. Such nucleic acids include siRNAs which target genes encoding keratin in the skin (Hickerson et al., 2006, *Ann. N.Y. Acad. Sci.*, 1082:56). In specific embodiments, such siRNAs may comprise one or more of any one of the following antisense sequences:

| | |
|---|---|
| AAACUUGUUUUUGAGGGUCU; | (SEQ ID NO.: 1) |
| UUUUUGAGGGUCUUGAUCU; | (SEQ ID NO.: 2) |
| UUUUGAGGGUCUUGAUCUGU; | (SEQ ID NO.: 3) |
| UUUGAGGGUCUUGAUCUGUU; | (SEQ ID NO.: 4) |
| AAGGAGGCAAACUUGUUUUU; | (SEQ ID NO.: 5) |
| AACUUGUUGAGGGUCUUGAU; | (SEQ ID NO.: 6) |
| AAACUUGUUGAGGGUCUUGU; and | (SEQ ID NO.: 7) |
| CAAACUUGUUGAGGGUCUUU | (SEQ ID NO.: 8) |

(Hickerson et al., 2006, *Ann. N.Y. Acad. Sci.*, 1082:56).

In some embodiments, nucleic acids to be used in accordance with the present invention suppress molecular pathways that cause skin inflammation. Such nucleic acids include cytidine-phosphate-guanosine oligodeoxynucleotides, including two cytidine-phosphate-guanosine (CpG) motifs (CpG-1-phosphorothioate (PTO)) and a poly-cytidine motif (Non-CpG-5-PTO) (Pivarcsi, 2007, *J. Invest. Dermatol.*, 127:846; and Dorn et al., 2007, *J. Invest. Dermatol.*, 127:746). In some embodiments, such nucleic acids may comprise phosphorothioate linkages. In some embodiments, such nucleic acids may comprise phosphodiester linkages. In specific embodiments, such nucleic acids may comprise one or more of any one of the following nucleotide sequences:

| | |
|---|---|
| TCCATGACGTTCCTGACGTT; | (SEQ ID NO.: 9) |
| TCCATGACGTTCCTGACGTT; | (SEQ ID NO.: 10) |
| TCCATGACGTTCCTGACGT; | (SEQ ID NO.: 11) |
| TCCATGACGTTCCTGACG; | (SEQ ID NO.: 12) |
| TCCTCGACGTCCCTGA; | (SEQ ID NO.: 13) |
| CATGACGTTCCT; | (SEQ ID NO.: 14) |
| GACGTT; and | (SEQ ID NO.: 15) |
| AACGTCAGGAACGTCATGGA | (SEQ ID NO.: 16) |

(Pivarcsi, 2007, *J. Invest. Dermatol.*, 127:846; and Dorn et al., 2007, *J. Invest. Dermatol.*, 127:746).

In some embodiments, nucleic acids to be used in accordance with the present invention may reduce VEGF production in the skin, which could have anti-angiogenesis therapeutic effects for conditions such as psoriasis. Such nucleic acids include a 19-mer antisense phosphorothioate oligodeoxynucleotide (complementary to bases 6-24 relative to the translational start site of the VEGFNPF mRNA) (Smyth et al., 1997, *J. Invest. Dermatol.*, 108:523). In specific embodiments, such nucleic acids may comprise one or more of any one of the following antisense nucleotide sequences:

| | |
|---|---|
| CACCCAAGACAGCAGAAAG; | (SEQ ID NO.: 17) |
| CTCCCAAGACAGCAGAAAG; | (SEQ ID NO.: 18) |
| CTGCCAAGACAGCAGAAAG; | (SEQ ID NO.: 19) |
| CACCCAACTCTCCAGAAAG; | (SEQ ID NO.: 20) |
| CACCCAAGACAGCAGAATG; and | (SEQ ID NO.: 21) |
| CACCCAAGACAGCAGATTG | (SEQ ID NO.: 22) |

(Smyth et al., 1997, *J. Invest. Dermatol.*, 108:523).

In some embodiments, nucleic acids to be used in accordance with the present invention may improve the DNA repair rate of skin damaged by UV radiation (e.g., UV radiation from sun exposure and/or sun burn). In some embodiments, nucleic acids to be used in accordance with the present invention may prevent or delay the onset of skin cancer. In some embodiments, nucleic acids to be used in accordance with the present invention may stimulate melanocyte production to result in tanning of the skin. In some embodiments, nucleic acids to be used in accordance with the present invention may achieve the appearance of tanning of the skin. Such nucleic acids may include dipyrimidine sequences (e.g., TT, TC, CT, CC). In some embodiments, such nucleic acids include thymidine dinucleotide (pTT), DNA oligonucleotides substantially homologous to the telomere 3' overhang sequence, and a 5'-phosphorylated 9 base oligonucleotide (p9 mer). In some embodiments, nucleic acids to be used in accordance with the present invention may treat various kinds of cancer (e.g., breast cancer, pancreatic cancer, ovarian cancer, melanoma, gliomas, etc.). Such nucleic acids include oligonucleotides substantially homologous to the telomere 3' overhang sequence. In specific embodiments, the telomere 3' overhang sequence comprises one or more of the following sequences: TTAGGG (SEQ ID NO.: 23); GTTAGGGTTAG (SEQ ID NO.: 24); GGTTAGGTGTAGGTTT (SEQ ID NO.: 25); GTTAGGGTT (SEQ ID NO.: 26); TTAGGGTTA (SEQ ID NO.: 27); GTTAGGTTTAAGGTT (SEQ ID NO.: 28); GGTAGGTGTAGGGTG (SEQ ID NO.: 29); GGTCGGTGTCGGGTG (SEQ ID NO.: 30); GGCAGGCGCAGGGCG (SEQ ID NO.: 31); GTTAGGGTTAGGGTT (SEQ ID NO.: 32); GATAAGGGATTGGGAT (SEQ ID NO.: 33); GAGTATGAG (SEQ ID NO.: 34); GGGTTAGGG (SEQ ID NO.: 35); GTTAGGGTTAG (SEQ ID NO.: 36); GGTAGGTGTAGGATT (SEQ ID NO.: 37); GGTAGGTGTAGGATTT (SEQ ID NO.: 38); GGTTAGGTGTAGGTTT (SEQ ID NO.: 39); GGTTAGGTGGAGGTTT (SEQ ID NO.: 40); GGTTAGGTTTAGGTTT (SEQ ID NO.: 41); GGTTAGGTTAAGGTTA (SEQ ID NO.: 42); GGTAGGTGTAGGGTG (SEQ ID NO.: 43); GTTAGGGTTAGGGTTA (SEQ ID NO.: 44); GGTTGGTTGGTTGGTT (SEQ ID NO.: 45); CCTTGGTTGGTTGGTTGGTT (SEQ ID NO.: 46); and GGTTGGTTGGTTGGTTGGTT (SEQ ID NO.: 47). In specific embodiments, the p9 mer comprises the following nucleotide sequence: pGAGTATGAG (SEQ ID NO.: 34) (Goukassian et al., 2004, *Proc. Natl. Acad. Sci., USA*, 101:3933; Arad et al., 2006, *FASEB* 1, 20:1895; Yaar et al., 2007, *Breast Cancer Res.*, 9:R13; Goukassian et al., 2002, *FASEB J.*, 16:754; and Ohashi et al., 2007, *J. Cell. Physiol.*, 210:582).

In some embodiments, nucleic acids to be used in accordance with the present invention may treat melanoma skin cancer (e.g., metastatic melanoma skin cancer). Such nucleic acids include a toll-like receptor 9-activating oligonucleotide (Pashenkov et al., 2006, *J. Clin. Oncol.*, 24:5716). In specific embodiments, such nucleic acids may comprise the following nucleotide sequence: TCGTCGTTTTGTCGTTTTGTCGTT (SEQ ID NO.: 48) (Pashenkov et al., 2006, *J. Clin. Oncol.*, 24:5716).

In some embodiments, a nucleic acid sequence that is homologous to any of the nucleic acids described herein may be used in accordance with the present invention. In some embodiments, nucleic acid sequences are considered to be "homologous" to one another if they comprise fewer than 30, 25, 20, 15, 10, 5, 4, 3, 2, or 1 nucleic acid substitutions relative to one another. In some embodiments, nucleic acid sequences are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, nucleic acid sequences are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Other Components

As indicated herein, nanoparticle compositions in accordance with the invention may contain or be combined with one or more other components. Certain exemplary such other components are discussed here.

Biologically Active Agents

It will be appreciated that nanoparticle compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a nanoparticle composition useful for treating tumors may be administered concurrently with another agent useful for treating tumors), or they may achieve different effects (e.g., control of any adverse effects).

By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, a nanoparticle composition may be administered concurrently with another therapeutic agent used to treat the same disorder), and/or they may achieve different effects (e.g., control of any adverse effects). In some embodiments, nanoparticle compositions of the invention are administered with a second therapeutic agent that is approved by the U.S. Food and Drug Administration.

In will further be appreciated that therapeutically active agents utilized "in combination" may be administered together in a single composition or administered separately in different compositions. For example, the present invention provides a composition comprising nanoparticles comprising a nucleic acid and a second biologically active agent to be delivered. The present invention also provides a composition comprising one population of nanoparticles comprising a nucleic acid to be delivered and a second population of nanoparticles comprising another biologically active agent to be delivered. The present invention also provides one composition comprising nanoparticles comprising a nucleic acid to be delivered and a second composition comprising nanoparticles comprising another biologically active agent to be delivered.

In general, it is expected that agents utilized in combination with be utilized at levels that do not exceed the levels at which they are utilized individually. In some embodiments, the levels utilized in combination will be lower than those utilized individually.

Any biologically active agents, including, for example, therapeutic, diagnostic, prophylactic, nutritional, cosmetic, and/or dermatological agents, may be delivered in combination with nucleic acids in accordance with the present invention. To give but a few examples, such biologically active agents may be small molecules, organometallic compounds, nucleic acids, proteins (including multimeric proteins, protein complexes, etc.), peptides, lipids, carbohydrates, herbs, hormones, metals, radioactive elements and compounds, drugs, vaccines, immunological agents, etc., and/or combinations thereof. Such biologically agents may be encapsulated within, adsorbed to the surface of, present at the interface of and/or present within a micellar membrane of one or more nanoparticles.

In some embodiments, the percent of biologically active agent in the composition used to prepare nanoparticles (e.g., in the premix) and/or in the nanoparticles ranges from 0.1%-25%. In some embodiments, the percentage of biologically active agent ranges from 0.1%-20%, from 0.1%-15%, from 0.1%-10%, from 0.1% -5%, or from 0.1%-1%. In some embodiments, the percentage of biologically active agent ranges from 1%-20%, from 5%-20%, from 10%-20%, from 15%-20%, or from 15%-25%. In some embodiments, the percentage of biologically active agent is less than 0.1%. In some embodiments, the percentage of biologically active agent is greater than 25%. In some embodiments, the percentage of biologically active agent is approximately 0.1%, approximately 0.5%, approximately 1%, approximately 2%, approximately 3%, approximately 4%, approximately 5%, approximately 6%, approximately 7%, approximately 8%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, or greater.

Relevant biologically active agents can be produced or obtained according to any available method or approach. Biologically active agents may contain, or be modified to contain, one or more moieties intended to facilitate their use or delivery in conjunction with nanoparticles in accordance with the invention. Such modification should not interfere with the biological activity of the agent. In some embodiments, the modification can optionally be removed in vivo. For example, biologically active agents may be detectably labeled and/or may be provided in a "pro" form that is converted or modified after delivery into an active form.

In some embodiments, the biologically active agent is a small molecule and/or organic compound with pharmaceutical activity. In some embodiments, the biologically active agent is a clinically-used drug. In some embodiments, the drug is an antibiotic, anti-viral agent, anesthetic, anticoagulant, anti-cancer agent, inhibitor of an enzyme, steroidal agent, anti-inflammatory agent, anti-neoplastic agent, anti-gen, vaccine, antibody, decongestant, antihypertensive, sedative, birth control agent, progestational agent, anticholinergic, analgesic, anti-depressant, anti-psychotic, β-adrenergic blocking agent, diuretic, cardiovascular active agent, vasoactive agent, non-steroidal anti-inflammatory agent, etc. Of particular interest are biologically active agents suitable for transdermal administration.

The biologically active agents delivered may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, the biologically active agent is a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, the biologically active agent is a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococccus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In some embodiments, the biologically active agent may be a protein. As used herein, the terms "protein" and "peptide" can be used interchangeably. In certain embodiments, peptides range from about 5 to about 100, about 10 to about 75, about 10 to about 50, about 10 to about 40, about 10 to about 35, about 15 to about 30, or about 20 to about 25 amino acids in size. Peptides from panels of peptides comprising random sequences and/or sequences which have been varied consistently to provide a maximally diverse panel of peptides may be used.

In some embodiments, the biologically active agent may be an antibody. In some embodiments, antibodies may include, but are not limited to, polyclonal, monoclonal, chimeric (e.g., "humanized"), single chain (recombinant) antibodies. In some embodiments, antibodies may have reduced effector functions and/or bispecific molecules. In some embodiments, antibodies may include Fab fragments and/or fragments produced by a Fab expression library.

In some embodiments, the biologically active agent is a nutraceutical agent. In some embodiments, the nutraceutical agent provides basic nutritional value. In some embodiments, the nutraceutical agent provides health or medical benefits. In some embodiments, the nutraceutical agent is a dietary supplement.

In some embodiments, the nutraceutical agent is a vitamin. In some embodiments, the vitamin is one or more of vitamin A (retinoids), vitamin B1 (thiamine), vitamin B2 (riboflavin), vitamin B3 (niacin), vitamin B5 (pantothenic acid), vitamin B6 (pyroxidone), vitamin B7 (biotin), vitamin B9 (folic acid), vitamin B12 (cyanocobalamin), vitamin C (ascorbic acid), vitamin D, vitamin E, or vitamin K.

In some embodiments, the nutraceutical agent is a mineral. In some embodiments, the mineral is one or more of bismuth, boron, calcium, chlorine, chromium, cobalt, copper, fluorine, iodine, iron, magnesium, manganese, molybdenum, nickel, phosphorus, potassium, rubidium, selenium, silicon, sodium, strontium, sulfur, tellurium, titanium, tungsten, vanadium, or zinc.

In some embodiments, the nutraceutical agent is an essential amino acid. In some embodiments, the amino acid is one or more of arginine, glutamine, histidine, isoleucine, leucine, lysine, methionine, phenylalanine, threonine, tryptophan, or valine.

In some embodiments, nutraceutical agents may include fatty acids and/or omega-3 fatty acids (e.g., DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g., cod liver oil), and probiotics. In some embodiments, nutraceutical agents may include bio-engineered foods genetically-engineered to have a desired property (also known as "pharmafoods").

Exemplary nutraceutical agents and dietary supplements are disclosed, for example, in Roberts et al., (*Nutraceuticals: The Complete Encyclopedia of Supplements, Herbs, Vitamins, and Healing Foods*, American Nutraceutical Association, 2001). Nutraceutical agents and dietary supplements are also disclosed in *Physicians' Desk Reference for Nutritional Supplements*, 1st Ed. (2001) and *The Physicians' Desk Reference for Herbal Medicines*, 1st Ed. (2001).

In some embodiments, nanoparticles in accordance with the invention loaded with nutraceutical agents can be incorporated into food substances. For example, the nutraceutical-loaded nanoparticles can be dissolved into liquids, such as beverages.

In some embodiments, the biologically active agent is a cosmetic and/or dermatological agent. In some embodiments, the cosmetic and/or dermatological agent may include vitamins and their derivatives (e.g., vitamin E and its esters, vitamin C and its esters, vitamins B, vitamin A alcohol or retinol and its esters), provitamins (e.g., panthenol, niacinamide or ergocalciferol), antioxidants, phenolic compounds (e.g., benzoyl peroxide), essential oils, humectants, sunscreen agents, moisturizing agents, proteins, ceramides, and pseudoceramides.

In some embodiments, a biologically active agent to be delivered with nucleic acids in accordance with the present invention may be one or more botulinum toxin peptides or protein complexes. In general, a botulinum toxin refers to any neurotoxin produced by *Clostridium botulinum*. In some embodiments, the botulinum toxin may be one or more of botulinum toxin serotypes A, B, $C_1$, $C_2$, D, E, F, or G. In some embodiments, botulinum toxin can refer to both a botulinum toxin complex (for example, the 300 kD, 600 kD, and 900 kD complexes) as well as purified (for example, isolated) botulinum toxin (for example, about 150 kD). In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

In some embodiments, the biologically active agent may be one or more therapeutic agents used in the treatment of cancer (e.g., chemotherapeutic agents). In specific embodiments, the biologically active anti-cancer agent to be delivered with nucleic acids in accordance with the present invention may be a cytotoxic agent. Most anti-cancer agents can be divided in to the following categories: alkylating agents, antimetabolites, natural products, and hormones and antagonists. Any of the anti-cancer agents discussed herein may be delivered in combination with nucleic acids in accordance with the present invention. Such combination therapy may be used to treat any type of cancer.

Anti-cancer agents typically affect cell division and/or DNA synthesis. However, some chemotherapeutic agents do not directly interfere with DNA. To give but one example, tyrosine kinase inhibitors (imatinib mesylate/GLEEVEC®) directly target a molecular abnormality in certain types of cancer (chronic myelogenous leukemia, gastrointestinal stromal tumors, etc.).

Alkylating agents are so named because of their ability to add alkyl groups to many electronegative groups under conditions present in cells. Alkylating agents typically function by chemically modifying cellular DNA. Exemplary alkylating agents include nitrogen mustards (e.g., mechlorethamine, cyclophosphamide, ifosfamide, melphalan (1-sarcolysin), chlorambucil), ethylenimines and methylmelamines (e.g., altretamine (hexamethylmelamine; HMM), thiotepa (triethylene thiophosphoramide), triethylenemelamine (TEM)), alkyl sulfonates (e.g., busulfan), nitrosureas (e.g., carmustine (BCNU), lomustine (CCMU), semustine (methyl-CCNU), streptozocin (streptozotocin)), and triazenes (e.g., dacarbazine (DTIC; dimethyltriazenoimidazolecarboxamide)).

Antimetabolites act by mimicking small molecule metabolites (e.g., folic acid, pyrimidines, and purines) in order to be incorporated into newly synthesized cellular DNA. Such agents also affect RNA synthesis. An exemplary folic acid analog is methotrexate (amethopterin). Exemplary pyrimidine analogs include fluorouracil (5-fluorouracil; 5-FU), floxuridine (fluorodeoxyuridine; FUdR), and cytarabine (cytosine arabinoside). Exemplary purine analogs include mercaptopurine (6-mercaptopurine; 6-MP), azathioprine, thioguanine (6-thioguanine; TG), fludarabine phosphate, pentostatin (2'-deoxycoformycin), cladribine (2-chlorodeoxyadenosine; 2-CdA), and erythrohydroxynonyladenine (EHNA).

Natural small molecule products which can be used as anti-cancer agents include plant alkaloids and antibiotics. Plant alkaloids and terpenoids (e.g., *vinca* alkaloids, podophyllotoxin, taxanes, etc.) typically block cell division by preventing microtubule function. *Vinca* alkaloids (e.g., vincristine, vinblastine (VLB), vinorelbine, vindesine, etc.) bind to tubulin and inhibit assembly of tubulin into microtubules. *Vinca* alkaloids are derived from the Madagascar periwinkle, *Catharanthus roseus* (formerly known as *Vinca rosea*). Podophyllotoxin is a plant-derived compound used to produce two other cytostatic therapeutic agents, etoposide and teniposide, which prevent cells from entering the G1 and S phases of the cell cycle. Podophyllotoxin is primarily obtained from the American Mayapple (*Podophyllum peltatum*) and a Himalayan Mayapple (*Podophyllum hexandrum*). Taxanes (e.g., paclitaxel, docetaxel, etc.) are derived from the Yew Tree. Taxanes enhance stability of microtubules, preventing the separation of chromosomes during anaphase.

Antibiotics which can be used as anti-cancer agents include dactinomycin (actinomycin D), daunorubicin (daunomycin; rubidomycin), doxorubicin, idarubicin, bleomycin, plicamycin (mithramycin), and mitomycin (mytomycin C).

Other small molecules which can be used as anti-cancer agents include platinum coordination complexes (e.g., cisplatin (cis-DDP), carboplatin), anthracenedione (e.g., mitoxantrone), substituted urea (e.g., hydroxyurea), methylhydrazine derivatives (e.g., procarbazine (N-methylhydrazine, MIH), and adrenocortical suppressants (e.g., mitotane (o,p'-DDD), aminoglutethimide).

Hormones which can be used as anti-cancer agents include adrenocorticosteroids (e.g., prednisone), aminoglutethimide, progestins (e.g., hydroxyprogesterone caproate, medroxyprogesterone acetate, megestrol acetate), estrogens (e.g., diethylstilbestrol, ethinyl estradiol), antiestrogen (e.g., tamoxifen), androgens (e.g., testosterone propionate, fluoxymesterone), antiandrogens (e.g., flutamide), and gonadotropin-releasing hormone analog (e.g., leuprolide).

Topoisomerase inhibitors act by inhibiting the function of topoisomerases, which are enzymes that maintain the topology of DNA. Inhibition of type I or type II topoisomerases interferes with both transcription and replication of DNA by upsetting proper DNA supercoiling. Some exemplary type I topoisomerase inhibitors include camptothecins (e.g., irinotecan, topotecan, etc.). Some exemplary type II topoisomerase inhibitors include amsacrine, etoposide, etoposide phosphate, teniposide, etc., which are semisynthetic derivatives of epipodophyllotoxins, discussed herein.

In specific embodiments, the biologically active anti-cancer agent may be an immunotherapeutic agent. Immunotherapy is the use of immune mechanisms against tumors which can be used in various forms of cancer, such as breast cancer (e.g., trastuzumab/HERCEPTIN®), leukemia (e.g., gemtuzumab ozogamicin/MYLOTARG®), and non-Hodgkin's lymphoma (e.g., rituximab/RITUXAN®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines (e.g., an HPV vaccine used for prophylaxis of cervical cancer).

Those skilled in the art will recognize that this is an exemplary, not comprehensive, list of biologically active agents that may be delivered in combination with nucleic acids in accordance with the present invention. Any biologically active agent may be encapsulated within or bound to the surface of nanoparticles in accordance with the invention. A more complete listing of classes and specific drugs suitable for use in the present invention may be found in *Pharmaceutical Drugs: Syntheses, Patents, Applications* by Axel Kleemann and Jurgen Engel, Thieme Medical Publishing, 1999 and the *Merck Index: An Encyclopedia of Chemicals, Drugs and Biologicals*, Ed. by Budavari et al., CRC Press, 1996, both of which are incorporated herein by reference.

Release Retarding Agents

In some embodiments, particularly those containing one or more biologically active agents (e.g., nucleic acids), nanoparticle compositions further include or are formulated with one or more release-retarding ingredients to allow for controlled release of the agent. Any release-retarding ingredient known in the art is suitable for use in making nanoparticles. In some embodiments, release-retarding ingredients are hydrophilic and/or hydrophobic polymers. Release-retarding ingredients include, for example celluloses or derivatives thereof, acrylic polymers, ester polymers, vinyl-pyrrolidone-based polymers, gums, other natural polymers, and/or combinations of these.

In some embodiments, the release-retarding ingredient is cellulose or a derivative thereof. In certain embodiments, the cellulose or derivative thereof comprises one or more of hydroxypropyl methylcellulose, methylcellulose, carboxymethylcellulose, sodium carboxymethylcellulose, hydroxypropyl ethylcellulose, hydroxyethylcellulose, and hydroxypropyl cellulose. In certain embodiments, the cellulose or derivative thereof is methylcellulose or a derivative thereof. In certain embodiments, the cellulose or derivative thereof is hydroxypropyl methylcellulose (HPMC). Those skilled in the art will appreciate that other cellulosic polymers, including other alkyl cellulosic polymers, can be utilized.

In some embodiments, the release-retarding ingredient is an acrylic polymer. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully polymerized copolymers of acrylic and methacrylic acid esters with a low content of quaternary ammonium groups.

In some embodiments, the release-retarding ingredient is a polyester. In some embodiments, polyesters include polyalkylene glycols, poly(glycolide-co-lactide), poly(lactic-co-glycolic acid)-PEG copolymer, poly(lactic acid), poly(lactic acid)-PEG copolymer, poly(glycolic acid), poly(glycolic acid)-PEG copolymer, co-polymers of polylactic and polyglycolic acid, and derivatives thereof. In some embodiments, polyesters include, for example, polyanhydrides, poly(ortho ester), poly(ortho ester)-PEG copolymer, poly(caprolactone), poly(caprolactone)-PEG copolymer, polyly-sine, polylysine-PEG copolymer, poly(ethylene imine), poly(ethylene imine)-PEG copolymer, and derivatives thereof. In some embodiments, polyesters include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

In some embodiments, the release-retarding ingredient is a cross-linked polymer of poly(vinyl-pyrrolidone). In some embodiments, the polymer is crospovidone. In some embodiments, the polymer is un-cross-linked poly(vinylpyrrolidone). In some embodiments, the polymer is povidone.

In some embodiments, the release-retarding ingredient may be a natural polymer. In some embodiments, the natural polymer is a gum, including, for example, xanthan gum, alginic acid, caraya gum, sodium alginate, and/or locust bean gum. In some embodiments, the natural polymer may be a protein (e.g., albumin), lipid, nucleic acid, or carbohydrate, and the release-retarding ingredient may be a polyester.

In some embodiments, the release-retarding ingredient is a cross-linked polymer of poly(vinyl-pyrrolidone). In some embodiments, the polymer is crospovidone. In some embodiments, the polymer is un-cross-linked poly(vinylpyrrolidone). In some embodiments, the polymer is povidone. In some embodiments, the release-retarding ingredient may be a natural polymer. In some embodiments, the natural polymer is a gum, including, for example, xanthan gum, alginic acid, caraya gum, sodium alginate, and/or locust bean gum. In some embodiments, the natural polymer may be a protein (e.g., albumin), lipid, nucleic acid, or carbohydrate.

Formulating Agents

Nanoparticle compositions in accordance with the invention may be formulated for administration to a subject. In certain embodiments, nanoparticle compositions are formulated for application to the skin, to achieve delivery (e.g., transdermal delivery) delivery to the subject. For example, nanoparticle compositions may be formulated in cosmetic or other preparations intended to be topically applied.

Human skin comprises the dermis and the epidermis. The epidermis has several layers of tissue, namely, stratum corneum, stratum lucidum, stratum granulosum, stratum spinosum, and stratum basale (identified in order from the outer surface of the skin inward). The stratum corneum presents the most significant hurdle in transdermal delivery of medications generally, and presumably of nucleic acids (e.g., modified or unmodified polynucleotides and/or nucleic acid residues, such as nucleotides, and/or nucleosides) in particular. The stratum corneum is typically about 10 μm to about 15 μm thick, and it consists of flattened, keratised cells (corneocytes) arranged in several layers. The intercellular space between the corneocytes is filled with lipidic structures, and may play an important role in the permeation of substances through skin (Bauerova et al., 2001, *European Journal of Drug Metabolism and Pharmacokinetics*, 26:85).

The rest of the epidermis below the stratum corneum is approximately 150 μm thick. The dermis is about 1 mm to about 2 mm thick and is located below the epidermis. The dermis is innervated by various capillaries as well as neuronal processes.

Traditionally, attempts at transdermal administration of medication have been focused in increasing the permeability of the stratum corneum. Some attempts have included using chemical enhancing agents that increase the permeability of molecules through the skin. Some attempts have included using mechanical apparatus to bypass or ablate portions of the stratum corneum. Some attempts have included using chemical or mechanical abrasive agents that increase the permeability of the skin. In addition, attempts have included use of ultrasound or iontophoresis to facilitate the permeation of pharmaceuticals through the skin. In most cases, the goal has been to a pharmaceutical agent, typically a small molecule, through the skin, typically so that an agent may pass to the capillary bed in the dermis where the agent may be systemically incorporated into the subject to achieve a therapeutic effect.

The present invention provides, among other things, methods of administering unmodified or modified nucleic acids (e.g., polynucleotides and/or nucleic acid residues, such as nucleotides and/or nucleosides) transdermally that do not require use of abrasive or other disrupting agents (whether chemical, mechanical, electrical, magnetic, etc.). Rather, the present inventors have surprisingly found that even large molecules (e.g., *botulinum* toxin) incorporated into nanoparticle compositions are effectively delivered transdermally without further steps to permeabilize or disrupt the stratum corneum.

The present invention therefore provides methods of administering nucleic acids through the topical application of a nanoparticle composition in accordance with the invention. In some embodiments, a nanoparticle composition is applied directly to the skin and for absorption through the epidermal layers. In some embodiments, the nanoparticle composition can penetrate the top layer of the skin, including the stratum corneum, dermal pores, and/or dermal glands, without the use of chemical or mechanical skin permeation enhancers or other agents that cause abrasion.

It will be appreciated by those of ordinary skill in the art that nanoparticle compositions for topical administration may be prepared as a cosmetic formulation such as skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, or dermatological composition such as lotions, ointments, gels, creams, patches or sprays.

Such formulation of nanoparticle compositions typically includes combination with one or more excipients such as, for example, fillers, sequestering agents, softeners, coloring materials (e.g., pigments and dyes), and fragrances.

In some embodiments, nanoparticle compositions are formulated as a cream. The term "cream" refers to a spreadable composition, typically formulated for application to the skin. Creams typically contain an oil and/or fatty acid based-matrix. Creams formulated according to the present invention may contain nanoparticles and may be capable of substantially complete penetration (e.g., of such nanoparticles) through the skin upon topical administration. Such a cream could also act as a carrier for incorporated materials (e.g., for example, for a nucleic acid).

Those of ordinary skill in the art will appreciate that nanoparticle compositions may be incorporated into a device such as, for example, a patch.

A variety of transdermal patch structures are known in the art; those of ordinary skill will appreciate that nanoparticle compositions may readily be incorporated into any of a variety of such structures. In some embodiments, a transdermal patch may further comprise a plurality of needles extending from one side of the patch that is applied to the skin, wherein the needles extend from the patch to project through the stratum corneum of the skin. In some embodiments, the needles do not rupture a blood vessel.

In some embodiments of the present invention, a nanoparticle composition can be provided in a depot in a patch so that pressure applied to the patch causes nucleic acids to be directed out of the patch (optionally through needles) and through the stratum corneum.

In some embodiments of the present invention, a transdermal patch includes an adhesive. Some examples of adhesive patches are well known (for example, see U.S. Design Pat. 296,006; and U.S. Pat. Nos. 6,010,715; 5,591,767; 5,008,110; 5,683,712; 5,948,433; and 5,965,154). Adhesive patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

Those of ordinary skill in the art will appreciate that a transdermal patch is but one example of a device with which nanoparticle compositions may be administered. To give but a few other examples, a device may be employed that allows the composition to be applied without first applying the composition to one's fingers, which may lead to undesirable biological effect on the fingers. Suitable devices include spatulas, swabs, syringes without needles, and adhesive patches. Use of spatulas or swabs, or the like may require the device to be inserted into a container containing the composition. Using syringes may be accomplished by filling the syringe with the composition. The composition may then be topically spread by the spatulas or swabs, or may be expelled from the syringes onto the patient's skin.

In some embodiments, it may be desirable to limit delivery of nucleic acids to only an intended delivery area. In some embodiments, such limited delivery may be accomplished by utilizing a nanoparticle composition in an application device that permits application of the composition to a target site on the skin without applying the composition to non-target site areas of the skin. Clearly, a transdermal patch may be utilized to this end. Alternatively or additionally, if nucleic acids are to be applied topically to only a selected area, other areas may be covered or pre-treated or otherwise protected from exposure.

Alternatively or additionally, nanoparticle compositions of the present invention may be administered by any other suitable means, including but not limited to, intravenous injection, intramuscular injection, subcutaneously injection, intraperitoneal injection, or infusion. In some embodiments, nanoparticle compositions of the present invention may be administered by intra-arterial injection, intraventricular injection, or intrathecal injection. In some embodiments, nanoparticle compositions of the present invention may be administered orally, interdermally, rectally, vaginally, mucosally, nasally, buccally, enterally, or sublingually. In some embodiments, nanoparticle compositions of the present invention may be administered by intratracheal instillation, bronchial instillation, and/or inhalation; and/or as an oral spray, nasal spray, and/or aerosol.

EXEMPLIFICATION

The following examples are only intended to provide illustrations of specific embodiments contemplated by the present invention. The examples are not intended in any way to be limiting.

Example 1

Adenosine Nanoparticle Formulation

Adenosine is a nucleotide that is known to have biological activity on skin structures (Brown et al., 2000, *J. Investig.*

*Dermatol.*, 115:849). An adenosine nanoparticle composition was prepared by forming a nanoemulsion. Briefly, 800 gm of 1349 medium chain triglyceride oil and 800 gm of TWEEN® 80 were stirred in a sterile vial for 5 minutes. 14 mg of adenosine (in 84 ml water) was added to the oil-TWEEN® mixture and stirred for 20 minutes. The sample was homogenized for 1 minute and then stirred for 20 minutes. The sample was microfluidized one time at 23,000 psi.

The resulting adenosine nanoemulsion was evaluated for particle size using the Malvern Nano S particle sizer capable of sizing particles between about 0.6 nm-6 µm. The nanoparticles formed were an average size of 75.9 nm in diameter. The nanoparticles had an average zeta potential of −12.9 mV.

The resulting nanoemulsion comprises a population of particles, and characteristics of the population of particles and of individual particles within the population were measured. 50% of the aggregate volume of all nanoparticles in the population were between 10 nm and 39.7 nm; 90% of all nanoparticles in the population were between 10 nm and 82.9 nm; and 95% of all nanoparticles in the population were between 10 nm and 113.0 nm. Therefore, the majority of particles in the population fell between the range of 10 nm and 85 nm.

Example 2

Phosphorylated Thymidine Dinucelotide (pTT) Nanoparticle Formulation

Phosphorylated thymidine dinucleotide (pTT) is known to have biological activity on skin structures (Goukassian et al., 2004, *Proc. Natl. Acad. Sci., USA*, 101:3933; Arad et al., 2006, *FASEB J.*, 20:1895; Yaar et al., 2007, *Breast Cancer Res.*, 9:R13; and Goukassian et al., 2002, *FASEB J.*, 16:754). For example, pTT stimulates melanocyte production to result in tanning of the skin or to achieve the appearance of tanning of the skin, a biological effect that can be assayed and measured visually.

A pTT nanoparticle composition is prepared by forming a nanoemulsion. Briefly, 800 mg of soybean oil and/or 1349 oil and 800 mg of TWEEN® 80 are stirred in a sterile vial for 5 minutes. 1 mg of pTT (in 8.4 ml water) is added to the oil-TWEEN® mixture and stirred for 20 minutes. The sample is homogenized for 1 minute and then stirred for 20 minutes. The sample is microfluidized one time at 23,000 psi.

The resulting pTT nanoemulsion is evaluated for particle size using the Malvern Nano S particle sizer. The majority of nanoparticles formed are between 50 nm and 150 nm in diameter.

Example 3

Skin Darkening Effects on Mice through Transdermal Application of a Nucleotide Nanoparticle This example demonstrates the biological efficacy on the skin of transdermal application of a nucleotide nanoparticle composition.

Methods

A nucleotide nanoemulsion prepared in accordance with Example 2 is mixed with an equal volume of a skin cream (i.e., Base PCCA Vanishing Cream Light) and then vortexed into a uniform cream to generate the "Treatment Cream."

A "Non-Nano Treatment Cream" is prepared by mixing the same amount of nucleotide into the same amount of water as Example 2 and then vortexing with the same amount of skin cream as is used to prepare the Treatment Cream. The Non-Nano Treatment Cream comprises all of the same components of the Treatment cream, but the preparation is not subjected to high shear force and, therefore, does not form a nanoemulsion. In contrast to the Treatment Cream, which is a nanoemulsion comprising a particular set of ingredients, the Non-Nano Treatment Cream is simply a combination of the same set of ingredients, and is not formulated as a nanoemulsion.

A "Control Cream" is prepared by vortexing the same amount of water as Example 2 and with the same amount of skin cream as is used to prepare the Treatment Cream. The Control Cream is not a nanoemulsion and does not contain the pTT active ingredient.

Thirty Swiss Webster mice are purchased that are each approximately 20 grams of weight. Upon arrival, all animals are acclimated to their cages for one week (group housed 10 mice per cage per group as defined below) and provided with standard cage bedding and Purina 5001 chow. After one week, the following treatment paradigms are applied:

Treatment Paradigms

Group 1 (Control): Each day for three weeks, 10 mice have 100 µl of Control Cream applied to each of their backs with a gloved finger until no cream is visible. The mice are shaved with an electric razor prior to the first treatment and at the beginning of each subsequent week.

Group 2 (Non-Nano Treatment): Each day for three weeks, 10 mice have 100 µl of Non-Nano Treatment Cream applied to each of their backs with a gloved finger until no cream is visible. The mice are shaved with an electric razor prior to the first treatment and at the beginning of each subsequent week.

Group 3 (Treatment): Each day for three weeks, 10 mice have 100 µl of Treatment Cream applied to each of their backs with a gloved finger until no cream is visible. The mice are shaved with an electric razor prior to the first treatment and at the beginning of each subsequent week.

Assessment

Prior to the initial treatment and each week thereafter, an observer blinded to the treatment status of the mice rates the skin tone of the treated area on the mouse back from not tan (0) to very tanned (5).

After three weeks, the animals are sacrificed, and skin from their backs is studied to determine potential treatment effects by comparing average measurements of each Group from skin dissected from the same region of each mouse's back. Melanocyte stimulation is assessed by examination of a histologic cross-section of the mouse back skin that will be microtomed, placed on a glass slide, a histologically stained. The number and degree of darkness of melanocytes is assessed by a pathologist blinded to the treatment status of the mice.

Results and Conclusion

The results are expected to show that, on average, the Treatment Group has statistically more tan skin than the Control Group and that of the Non-Nano Treatment Group. The results are expected to show that, on average, the Treatment Group has statistically more melanocyte stimulation than the Control Group and the Non-Nano Treatment Group as measured by the pathologist's assessment of the histologically stained slides.

In sum, these controlled data are expected to show that the topical nucleotide nanoemulsion preparation has a measurable biological effect on the skin when compared to a control cream without such a nucleotide. The data are expected to show that the nucleotide nanoemulsion has a biological effect that is measurably greater than simple cream with the same nucleotide that was not in a nanoparticle formulation.

Equivalents and Scope

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as “a,” “an,” and “the” may mean one or more than one unless indicated to the contrary or otherwise evident from the context. Thus, for example, reference to “a nanoparticle” includes a plurality of such nanoparticle, and reference to “the cell” includes reference to one or more cells known to those skilled in the art, and so forth. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term “comprising” is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid, any polynucleotide, any nucleic acid residue, any nucleotide modification, any oil, any surfactant, any amphiphilic entity, any biologically active agent, any method of treatment, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A method, comprising the steps of:
providing a composition comprising a nanoemulsion comprising particles in a dispersion medium, wherein the nanoemulsion was generated by exposure to high shear force; wherein:
the nanoemulsion comprises an oil and a surfactant;
the majority of particles in the dispersion medium are nanoparticles that have diameters between approximately 10 nanometers and approximately 300 nanometers;
the particles comprise at least one nucleic acid of length up to 30 nucleotides that has biological activity in the skin, subcutaneous tissue, contiguous muscle, or distant tissue;
wherein the at least one nucleic acid comprises a thymidine dinucleotide, a phosphorylated thymidine dinucleotide (pTT), or a combination of both; and
the at least one nucleic acid does not induce immune reactions; and
administering the composition to the skin of a subject so that transdermal delivery of the nucleic acid is achieved; and wherein at least 95% of the nucleic acid penetrates the skin.

2. The method of claim 1, wherein the composition is administered transdermally using an adhesive patch.

3. The method of claim 1, wherein the composition is administered transdermally using a spatula, swab, syringe without a needle, gloved finger, or unprotected finger.

4. The method of claim 1, wherein the composition is administered transdermally using a device that permits application of the composition to a target site on the skin without applying the composition to non-target sites of the skin.

5. The method of claim 1, wherein the composition is administered so that a cosmetic effect is achieved.

6. The method of claim 5, wherein the cosmetic effect is or comprises tanning of the skin.

7. The method of claim 1, wherein the biological activity is activity on skin structures.

8. The method of claim 1, wherein the biological activity of the nucleic acid is not impaired by the nanoparticles.

9. The method of claim 1, wherein the majority of particles have a range of diameters between approximately 10 nanometers and approximately 200 nanometers.

10. The method of claim 9, wherein the majority of particles have a range of diameters between approximately 10 nanometers and approximately 120 nanometers.

11. The method of claim 10, wherein the majority of particles have a range of diameters between approximately 10 nanometers and approximately 50 nanometers.

12. The method of claim 1,
wherein the oil is selected from the group consisting of saturated and unsaturated almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils; butyl stearate; caprylic triglyceride; capric triglyceride; cyclomethicone; diethyl sebacate; dimethicone 360; isopropyl myristate; medium chain triglycerides; mineral oil; octyldodecanol; oleyl alcohol; and silicone oil; and wherein the surfactant is selected from the group consisting of phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (SPAN®85) glycocholate; sorbitan monolaurate (SPAN®20); polysorbate 20 (TWEEN®20); polysorbate 60 (TWEEN®60); polysorbate 65 (TWEEN®65); polysorbate 80 (TWEEN®80); polysorbate 85 (TWEEN®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; and ion pairing agents.

13. The method of claim 1, wherein the nanoemulsion comprises a pre-mix of a medium chain triglyceride, Tween, water, and the nucleic acid.

14. The method of claim 1, wherein the nucleic acid is encapsulated within the nanoparticles.

15. The method of claim 1, wherein the nucleic acid is associated with the particle surface.

16. The method of claim 1, wherein the nanoemulsion can penetrate skin without altering or changing the skin.

17. The method of claim 1, wherein the nanoemulsion can penetrate skin without the use of skin permeation enhancers or abrasives.

18. The method of claim 1, wherein the nanoemulsion can penetrate the top layer of skin without the use of skin permeation enhancers or abrasives.

19. The method of claim 1, wherein the oil and surfactant are present in a ratio ranging from 0.5-2.0.

20. The method of claim 1, wherein the percent of oil in the nanoemulsion ranges from 1%-30%.

21. The method of claim 1, wherein the percent of oil in the nanoemulsion ranges from approximately 5% to approximately 9%.

22. The method of claim 1, wherein the percent of surfactant in the nanoemulsion ranges from 1%-30%.

23. The method of claim 1, wherein the percent of surfactant in the nanoemulsion ranges from approximately 5% to approximately 9%.

24. The method of claim 1, wherein the nanoemulsion is substantially free of toxic solvents.

25. The method of claim 1, wherein the nanoparticles further comprise an additional biologically active agent.

26. The method of claim 25, wherein the additional biologically active agent is a chemotherapeutic agent.

27. The method of claim 26, wherein the additional biologically active agent is dacarbazine.

28. The method of claim 1, wherein the composition comprises a second population of particles comprising a chemotherapeutic agent.

29. The method of claim 28, wherein the chemotherapeutic agent is dacarbazine.

30. The method of claim 1, wherein the at least one nucleic acid is a single-stranded nucleic acid.

31. The method of claim 1, wherein the nanoemulsion comprises oily particles dispersed within an aqueous medium.

32. The method of claim 1, wherein the nanoemulsion comprises aqueous particles dispersed within an oily medium.

* * * * *

SEQUENCE LISTING

```
<160> NUMBER OF SEQ ID NOS: 48

<210> SEQ ID NO 1
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 1
aaacuuguuu uugagggucu                                             20

<210> SEQ ID NO 2
<211> LENGTH: 19
<212> TYPE: RNA
<213> ORGANISM: Artificial sequence
<220> FEATURE:
<223> OTHER INFORMATION: siRNA antisense sequence
```

<400> SEQUENCE: 2
uuuuugaggg ucuugaucu                                                    19

<210> SEQ ID NO 3
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 3
uuuugagggu cuugaucugu                                                   20

<210> SEQ ID NO 4
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 4
uuugaggguc uugaucuguu                                                   20

<210> SEQ ID NO 5
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 5
aaggaggcaa acuuguuuuu                                                   20

<210> SEQ ID NO 6
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 6
aacuuguuga gggucuugau                                                   20

<210> SEQ ID NO 7
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 7
aaacuuguug agggucuugu                                                   20

<210> SEQ ID NO 8
<211> LENGTH: 20
<212> TYPE: RNA
<213> ORGANISM: Artificial sequence
<220> FEATURE:
<223> OTHER INFORMATION: siRNA antisense sequence

<400> SEQUENCE: 8
caaacuuguu gagggucuuu                                                   20

<210> SEQ ID NO 9

```
<211> LENGTH: 20
<212> TYPE: DNA
<213> ORGANISM: Artificial sequence
<220> FEATURE:
<223> OTHER INFORMATION: DNA with CpG motif

<400> SEQUENCE: 9
tccatgacgt tcctgacgtt                                              20

<210> SEQ ID NO 10
<211> LENGTH: 20
<212> TYPE: DNA
<213> ORGANISM: Artificial sequence
<220> FEATURE:
<223> OTHER INFORMATION: DNA with CpG motif

<400> SEQUENCE: 10
tccatgacgt tcctgacgtt                                              20

<210> SEQ ID NO 11
<211> LENGTH: 19
<212> TYPE: DNA
<213> ORGANISM: Artificial sequence
<220> FEATURE:
<223> OTHER INFORMATION: DNA with CpG motif

<400> SEQUENCE: 11
tccatgacgt tcctgacgt                                               19

<210> SEQ ID NO 12
<211> LENGTH: 18
<212> TYPE: DNA
<213> ORGANISM: Artificial sequence
<220> FEATURE:
<223> OTHER INFORMATION: DNA with CpG motif

<400> SEQUENCE: 12
tccatgacgt tcctgacg                                                18

<210> SEQ ID NO 13
<211> LENGTH: 16
<212> TYPE: DNA
<213> ORGANISM: Artificial sequence
<220> FEATURE:
<223> OTHER INFORMATION: DNA with CpG motif

<400> SEQUENCE: 13
tcctcgacgt ccctga                                                  16

<210> SEQ ID NO 14
<211> LENGTH: 12
<212> TYPE: DNA
<213> ORGANISM: Artificial sequence
<220> FEATURE:
<223> OTHER INFORMATION: DNA with CpG motif

<400> SEQUENCE: 14
catgacgttc ct                                                      12

<210> SEQ ID NO 15
<211> LENGTH: 6
<212> TYPE: DNA
<213> ORGANISM: Artificial sequence
<220> FEATURE:
<223> OTHER INFORMATION: DNA with CpG motif

<400> SEQUENCE: 15
```

```
gacgtt                                                              6

<210> SEQ ID NO 16
<211> LENGTH: 20
<212> TYPE: DNA
<213> ORGANISM: Artificial sequence
<220> FEATURE:
<223> OTHER INFORMATION: DNA with CpG motif

<400> SEQUENCE: 16
aacgtcagga acgtcatgga                                              20

<210> SEQ ID NO 17
<211> LENGTH: 19
<212> TYPE: DNA
<213> ORGANISM: Artificial sequence
<220> FEATURE:
<223> OTHER INFORMATION: VEGF/VPF antisense

<400> SEQUENCE: 17
cacccaagac agcagaaag                                               19

<210> SEQ ID NO 18
<211> LENGTH: 19
<212> TYPE: DNA
<213> ORGANISM: Artificial sequence
<220> FEATURE:
<223> OTHER INFORMATION: VEGF/VPF antisense

<400> SEQUENCE: 18
ctcccaagac agcagaaag                                               19

<210> SEQ ID NO 19
<211> LENGTH: 19
<212> TYPE: DNA
<213> ORGANISM: Artificial sequence
<220> FEATURE:
<223> OTHER INFORMATION: VEGF/VPF antisense

<400> SEQUENCE: 19
ctgccaagac agcagaaag                                               19

<210> SEQ ID NO 20
<211> LENGTH: 19
<212> TYPE: DNA
<213> ORGANISM: Artificial sequence
<220> FEATURE:
<223> OTHER INFORMATION: VEGF/VPF antisense

<400> SEQUENCE: 20
cacccaactc tccagaaag                                               19

<210> SEQ ID NO 21
<211> LENGTH: 19
<212> TYPE: DNA
<213> ORGANISM: Artificial sequence
<220> FEATURE:
<223> OTHER INFORMATION: VEGF/VPF antisense

<400> SEQUENCE: 21
cacccaagac agcagaatg                                               19

<210> SEQ ID NO 22
<211> LENGTH: 19
<212> TYPE: DNA
```

```
<213> ORGANISM: Artificial sequence
<220> FEATURE:
<223> OTHER INFORMATION: VEGF/VPF antisense

<400> SEQUENCE: 22
cacccaagac agcagattg                                                    19

<210> SEQ ID NO 23
<211> LENGTH: 6
<212> TYPE: DNA
<213> ORGANISM: Artificial sequence
<220> FEATURE:
<223> OTHER INFORMATION: telomere 3' overhang sequence

<400> SEQUENCE: 23 ttaggg                                                                   6

<210> SEQ ID NO 24
<211> LENGTH: 11
<212> TYPE: DNA
<213> ORGANISM: Artificial sequence
<220> FEATURE:
<223> OTHER INFORMATION: telomere 3' overhang sequence

<400> SEQUENCE: 24
gttagggtta g                                                            11

<210> SEQ ID NO 25
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 25
ggttaggtgt aggttt                                                       16

<210> SEQ ID NO 26
<211> LENGTH: 9
<212> TYPE: DNA
<213> ORGANISM: Artificial sequence
<220> FEATURE:
<223> OTHER INFORMATION: telomere 3' overhang sequence

<400> SEQUENCE: 26 gttagggtt                                                                9

<210> SEQ ID NO 27
<211> LENGTH: 9
<212> TYPE: DNA
<213> ORGANISM: Artificial sequence
<220> FEATURE:
<223> OTHER INFORMATION: telomere 3' overhang sequence

<400> SEQUENCE: 27 ttagggtta                                                                9

<210> SEQ ID NO 28
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 28
gttaggttta aggtt                                                        15
```

<210> SEQ ID NO 29
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 29
ggtaggtgta gggtg                                               15

<210> SEQ ID NO 30
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 30
ggtcggtgtc gggtg                                               15

<210> SEQ ID NO 31
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 31
ggcaggcgca gggcg                                               15

<210> SEQ ID NO 32
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 32
gttagggtta gggtt                                               15

<210> SEQ ID NO 33
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 33
gataagggat tgggat                                              16

<210> SEQ ID NO 34
<211> LENGTH: 9
<212> TYPE: DNA
<213> ORGANISM: Artificial sequence
<220> FEATURE:
<223> OTHER INFORMATION: telomere 3' overhang sequence

<400> SEQUENCE: 34 gagtatgag                                                       9

<210> SEQ ID NO 35
<211> LENGTH: 9
<212> TYPE: DNA
<213> ORGANISM: Artificial sequence
<220> FEATURE:

-continued

```
<223> OTHER INFORMATION: telomere 3' overhang sequence

<400> SEQUENCE: 35 gggttaggg                                                                 9

<210> SEQ ID NO 36
<211> LENGTH: 11
<212> TYPE: DNA
<213> ORGANISM: Artificial sequence
<220> FEATURE:
<223> OTHER INFORMATION: telomere 3' overhang sequence

<400> SEQUENCE: 36
gttagggtta g                                                             11

<210> SEQ ID NO 37
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 37
ggtaggtgta ggatt                                                         15

<210> SEQ ID NO 38
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 38
ggtaggtgta ggattt                                                        16

<210> SEQ ID NO 39
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 39
ggttaggtgt aggttt                                                        16

<210> SEQ ID NO 40
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 40
ggttaggtgg aggttt                                                        16

<210> SEQ ID NO 41
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 41
ggttaggttt aggttt                                                        16
```

```
<210> SEQ ID NO 42
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 42
ggttaggtta aggtta                                                    16

<210> SEQ ID NO 43
<211> LENGTH: 15
<212> TYPE: DNA
<213> ORGANISM: Artificial sequence
<220> FEATURE:
<223> OTHER INFORMATION: telomere 3' overhang sequence

<400> SEQUENCE: 43
ggtaggtgta gggtg                                                     15

<210> SEQ ID NO 44
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 44
gttagggtta gggtta                                                    16

<210> SEQ ID NO 45
<211> LENGTH: 16
<212> TYPE: DNA
<213> ORGANISM: Artificial sequence
<220> FEATURE:
<223> OTHER INFORMATION: telomere 3' overhang sequence

<400> SEQUENCE: 45
ggttggttgg ttggtt                                                    16

<210> SEQ ID NO 46
<211> LENGTH: 20
<212> TYPE: DNA
<213> ORGANISM: Artificial sequence
<220> FEATURE:
<223> OTHER INFORMATION: telomere 3' overhang sequence

<400> SEQUENCE: 46
ccttggttgg ttggttggtt                                                20

<210> SEQ ID NO 47
<211> LENGTH: 20
<212> TYPE: DNA
<213> ORGANISM: Artificial sequence
<220> FEATURE:
<223> OTHER INFORMATION: telomere 3' overhang sequence

<400> SEQUENCE: 47
ggttggttgg ttggttggtt                                                20

<210> SEQ ID NO 48
<211> LENGTH: 24
<212> TYPE: DNA
<213> ORGANISM: Artificial sequence
<220> FEATURE:
<223> OTHER INFORMATION: toll-like receptor 9-activating oligonucleotide
```

<400> SEQUENCE: 48
tcgtcgtttt gtcgttttgt cgtt                24